United States Patent
Halasz et al.

(10) Patent No.: US 10,590,192 B2
(45) Date of Patent: Mar. 17, 2020

(54) MIDKINE ANTIBODY

(71) Applicant: Cellmid Limited, New South Wales (AU)

(72) Inventors: Maria Halasz, New South Wales (AU); Darren Jones, New South Wales (AU); Nico Mertens, Hertfordshire (GB); Phillip Cunnah, Porto Salvo (PT)

(73) Assignee: CELLMID LIMITED (AU)

( * ) Notice: Subject to any disclaimer, the term of this patent is extended or adjusted under 35 U.S.C. 154(b) by 257 days.

(21) Appl. No.: 15/518,849

(22) PCT Filed: Oct. 14, 2015

(86) PCT No.: PCT/AU2015/050629
§ 371 (c)(1),
(2) Date: Apr. 13, 2017

(87) PCT Pub. No.: WO2016/058047
PCT Pub. Date: Apr. 21, 2016

(65) Prior Publication Data
US 2017/0240628 A1    Aug. 24, 2017

(30) Foreign Application Priority Data

Oct. 14, 2014 (AU) ............................. 2014904102

(51) Int. Cl.
*C07K 16/00* (2006.01)
*A61K 39/395* (2006.01)
*C07K 16/22* (2006.01)
*G01N 33/68* (2006.01)
*G01N 33/574* (2006.01)
*A61K 31/555* (2006.01)
*C07K 16/30* (2006.01)
*G01N 33/74* (2006.01)

(52) U.S. Cl.
CPC ............ *C07K 16/22* (2013.01); *A61K 31/555* (2013.01); *A61K 39/3955* (2013.01); *A61K 39/39558* (2013.01); *C07K 16/30* (2013.01); *G01N 33/57407* (2013.01); *G01N 33/57434* (2013.01); *G01N 33/57488* (2013.01); *G01N 33/6893* (2013.01); *G01N 33/74* (2013.01); *C07K 2317/24* (2013.01); *C07K 2317/55* (2013.01); *C07K 2317/56* (2013.01); *C07K 2317/626* (2013.01); *C07K 2317/76* (2013.01); *C07K 2317/92* (2013.01); *G01N 2333/475* (2013.01)

(58) Field of Classification Search
None
See application file for complete search history.

(56) References Cited

U.S. PATENT DOCUMENTS

| 5,530,101 | A | * | 6/1996 | Queen | C07K 16/00 424/133.1 |
| 2010/0092488 | A1 | * | 4/2010 | Suzumura | A61K 31/7105 424/172.1 |
| 2010/0311187 | A1 | * | 12/2010 | Matsui | C07K 16/22 436/501 |
| 2015/0203573 | A1 | | 7/2015 | Kadomatsu et al. | |

FOREIGN PATENT DOCUMENTS

| WO | 2008/059616 A1 | 5/2008 | |
| WO | 2012/122590 A1 | 9/2012 | |
| WO | WO 2012122590 | * 9/2012 | ........... A61K 39/395 |
| WO | 2014/021339 A1 | 2/2014 | |

OTHER PUBLICATIONS

Paul, Fundamental Immunology, 3rd Edition, 1993, pp. 292-295.*
Rudikoff et al, Proc. Natl. Acad. Sci. USA, 79(6):1979-1983, Mar. 1982.*
Colman P. M., Research in Immunology, 145:33-36, 1994.*
MacCallum et al, J. Mol. Biol., 262, 732-745, 1996.*
Pascalis et al, Journal of Immunology, 2002, vol. 169, pp. 3076-3084.*
European Search Report dated Feb. 19, 2018 in corresponding European Application No. 15849875.8.
Yao et al., "Preparation and Preliminary Characterization of Rabbit Monoclonal Antibodies Against Human Midkine", Hybridoma 30(1), pp. 87-93 (2011).
Inoh et al., "Doxorubicin-Conjugated Anti-Midkine Monoclonal Antibody as a Potential Anti-Tumor Drug", Jpn. J. Cli. Oncol. 36(4):207-211 (2006).

* cited by examiner

*Primary Examiner* — Mark Halvorson
(74) *Attorney, Agent, or Firm* — Riverside Law LLP

(57) ABSTRACT

The present disclosure is directed to isolated or recombinant proteins, such as antibodies, which bind to, and inhibit or reduce the function of, midkine (MK) and their use as therapeutic and/or diagnostic agents for midkine-related disorders. The present disclosure is also related to nucleic acid sequences which encode said proteins and their expression in recombinant host cells. In particular, the present disclosure is directed towards humanized antibodies derived from murine antibody IP14 which specifically bind to human MK.

Figure 1:
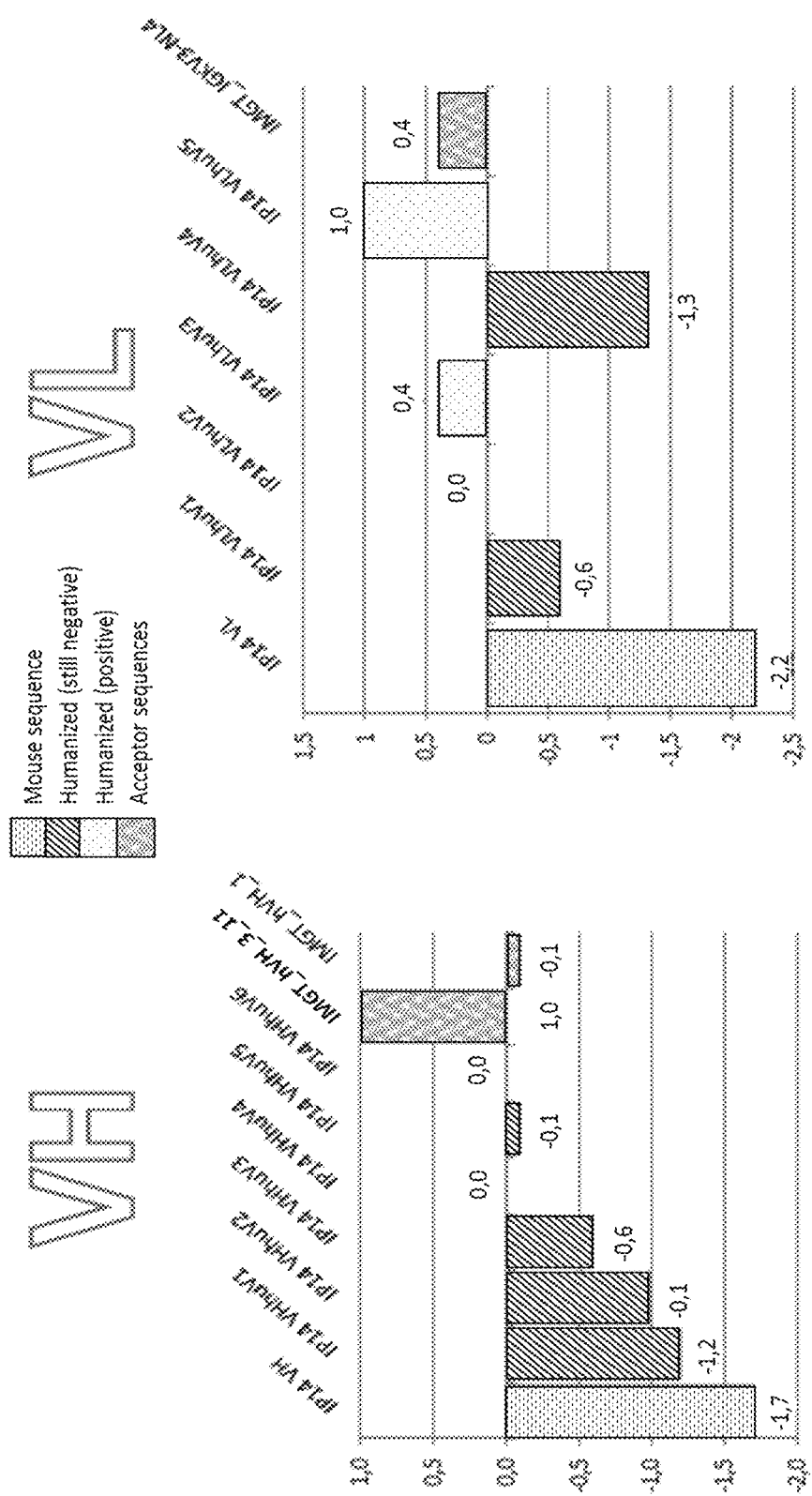

32 Claims, 6 Drawing Sheets
Specification includes a Sequence Listing.

SEQUENCE LISTING

```
<160> NUMBER OF SEQ ID NOS: 25

<210> SEQ ID NO 1
<211> LENGTH: 117
<212> TYPE: PRT
<213> ORGANISM: Mouse

<400> SEQUENCE: 1

Gln Val Gln Leu Gln Gln Pro Gly Ala Glu Leu Val Arg Pro Gly His
1               5                   10                  15

Ser Val Lys Leu Ser Cys Lys Ala Ser Gly Gln Ser Phe Ser Ser Tyr
            20                  25                  30

Trp Met Asn Trp Val Arg Gln Arg Pro Gly Gln Gly Leu Glu Trp Ile
        35                  40                  45

Gly Met Ile His Pro Ser Asp Ser Glu Thr Ile Leu Asn Gln Lys Phe
    50                  55                  60

Lys Asp Lys Ala Thr Leu Thr Val Asp Ile Ser Ser Asn Thr Ala Tyr
65                  70                  75                  80

Met Gln Leu Ser Ser Pro Thr Ser Glu Asp Ser Ala Val Tyr Phe Cys
                85                  90                  95

Ser Ser Trp Ser Ala Lys Arg Gly Asp Phe Trp Gly Gln Gly Thr Thr
            100                 105                 110

Leu Thr Val Ser Ser
        115

<210> SEQ ID NO 2
<211> LENGTH: 117
<212> TYPE: PRT
<213> ORGANISM: Artificial sequence
<220> FEATURE:
<223> OTHER INFORMATION: Variable region heavy chain humanised variant 1
      (VH1)

<400> SEQUENCE: 2
```

Gln Val Gln Leu Val Gln Ser Gly Ala Glu Val Lys Lys Pro Gly His
1               5                   10                  15

Ser Val Lys Val Ser Cys Lys Ala Ser Gly Gln Ser Phe Ser Ser Tyr
            20                  25                  30

Trp Met Asn Trp Val Arg Gln Ala Pro Gly Gln Gly Leu Glu Trp Ile
        35                  40                  45

Gly Met Ile His Pro Ser Asp Ser Glu Thr Ile Leu Asn Gln Lys Phe
    50                  55                  60

Lys Asp Lys Ala Thr Leu Thr Val Asp Ile Ser Thr Ser Thr Ala Tyr
65                  70                  75                  80

Met Glu Leu Ser Ser Pro Arg Ser Glu Asp Thr Ala Val Tyr Tyr Cys
                85                  90                  95

Ser Ser Trp Ser Ala Lys Arg Gly Asp Phe Trp Gly Gln Gly Thr Leu
            100                 105                 110

Val Thr Val Ser Ser
        115

<210> SEQ ID NO 3
<211> LENGTH: 117
<212> TYPE: PRT
<213> ORGANISM: Artificial sequence
<220> FEATURE:
<223> OTHER INFORMATION: Variable region heavy chain humanised variant 2
      (VH2)

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Gln Ser Phe Ser Ser Tyr
            20                  25                  30

Trp Met Asn Trp Val Arg Gln Ala Pro Gly Gln Gly Leu Glu Trp Ile
        35                  40                  45

Gly Met Ile His Pro Ser Asp Ser Glu Thr Ile Leu Asn Gln Lys Phe
    50                  55                  60

Lys Asp Lys Ala Thr Leu Thr Val Asp Ile Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Ser Trp Ser Ala Lys Arg Gly Asp Phe Trp Gly Gln Gly Thr Leu
            100                 105                 110

Val Thr Val Ser Ser
        115

<210> SEQ ID NO 4
<211> LENGTH: 117
<212> TYPE: PRT
<213> ORGANISM: Artificial sequence
<220> FEATURE:
<223> OTHER INFORMATION: Variable region heavy chain humanised variant 3
      (VH3)

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Gln Ser Phe Ser Ser Tyr
            20                  25                  30

Trp Met Asn Trp Val Arg Gln Ala Pro Gly Gln Gly Leu Glu Trp Met
        35                  40                  45

```
Gly Met Ile His Pro Ser Asp Ser Glu Thr Ile Leu Asn Gln Lys Phe
        50                  55                  60

Lys Asp Lys Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Trp Ser Ala Lys Arg Gly Asp Phe Trp Gly Gln Gly Thr Leu
                100                 105                 110

Val Thr Val Ser Ser
        115

<210> SEQ ID NO 5
<211> LENGTH: 117
<212> TYPE: PRT
<213> ORGANISM: Artificial sequence
<220> FEATURE:
<223> OTHER INFORMATION: Variable region heavy chain humanised variant 4
      (VH4)

<400> SEQUENCE: 5

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile His Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Trp Ser Ala Lys Arg Gly Asp Phe Trp Gly Gln Gly Thr Leu
                100                 105                 110

Val Thr Val Ser Ser
        115

<210> SEQ ID NO 6
<211> LENGTH: 117
<212> TYPE: PRT
<213> ORGANISM: Artificial sequence
<220> FEATURE:
<223> OTHER INFORMATION: Variable region heavy chain humanised variant 5
      (VH5)

<400> SEQUENCE: 6

Gln Val Gln Leu Val Gln Ser Gly Gly Gly Leu Val Gln Pro Gly Gly
 1               5                  10                  15

Ser Leu Arg Leu Ser Cys Ala Ala Ser Gly Gln Ser Phe Ser Ser Tyr
                 20                  25                  30

Trp Met Asn Trp Val Arg Gln Ala Pro Gly Gln Gly Leu Glu Trp Ile
             35                  40                  45

Gly Met Ile His Pro Ser Asp Ser Glu Thr Ile Leu Asn Gln Lys Phe
        50                  55                  60

Lys Asp Lys Ala Thr Leu Thr Val Asp Ile Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95
```

```
Ser Ser Trp Ser Ala Lys Arg Gly Asp Phe Trp Gly Gln Gly Thr Leu
            100                 105                 110

Val Thr Val Ser Ser
        115

<210> SEQ ID NO 7
<211> LENGTH: 117
<212> TYPE: PRT
<213> ORGANISM: Artificial sequence
<220> FEATURE:
<223> OTHER INFORMATION: Variable region heavy chain humanised variant 6
      (VH6)

<400> SEQUENCE: 7

Gln Val Gln Leu Val Gln Ser Gly Gly Gly Leu Val Lys Pro Gly His
1               5                   10                  15

Ser Leu Arg Leu Ser Cys Ala Ala Ser Gly Gln Ser Phe Ser Ser Tyr
            20                  25                  30

Trp Met Asn Trp Val Arg Gln Ala Pro Gly Lys Gly Leu Glu Trp Ile
        35                  40                  45

Gly Met Ile His Pro Ser Asp Ser Glu Thr Ile Leu Asn Gln Lys Phe
    50                  55                  60

Lys Asp Lys Ala Thr Leu Ser Val Asp Ile Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ser Ser Trp Ser Ala Lys Arg Gly Asp Phe Trp Gly Gln Gly Thr Leu
            100                 105                 110

Val Thr Val Ser Ser
        115

<210> SEQ ID NO 8
<211> LENGTH: 117
<212> TYPE: PRT
<213> ORGANISM: Artificial sequence
<220> FEATURE:
<223> OTHER INFORMATION: Consensus sequence for VH5/6
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 8

Gln Val Gln Leu Val Gln Ser Gly Gly Gly Leu Val Xaa Pro Gly Xaa
1               5                   10                  15

Ser Leu Arg Leu Ser Cys Ala Ala Ser Gly Gln Ser Phe Ser Ser Tyr
```

```
                20                  25                  30
Trp Met Asn Trp Val Arg Gln Ala Pro Gly Xaa Gly Leu Glu Trp Ile
            35                  40                  45
Gly Met Ile His Pro Ser Asp Ser Glu Thr Ile Leu Asn Gln Lys Phe
        50                  55                  60
Lys Asp Lys Ala Thr Leu Xaa Val Asp Ile Xaa Lys Asn Xaa Ala Tyr
 65                 70                  75                  80
Leu Gln Met Asn Ser Leu Arg Ala Glu Asp Thr Ala Val Tyr Tyr Cys
                85                  90                  95
Ser Ser Trp Ser Ala Lys Arg Gly Asp Phe Trp Gly Gln Gly Thr Leu
            100                 105                 110
Val Thr Val Ser Ser
            115

<210> SEQ ID NO 9
<211> LENGTH: 108
<212> TYPE: PRT
<213> ORGANISM: Mouse

<400> SEQUENCE: 9

Asp Ile Val Leu Thr Gln Ser Pro Ala Thr Leu Ser Val Thr Pro Gly
 1               5                  10                  15
Asp Ser Val Asn Leu Ser Cys Arg Ala Ser Glu Ser Ile Ser Asn Asn
                20                  25                  30
Leu His Trp Tyr Gln Gln Lys Ser His Glu Ser Pro Arg Leu Leu Ile
            35                  40                  45
Lys Tyr Ala Ser Gln Ser Ile Ser Gly Ile Pro Ser Arg Phe Ser Gly
        50                  55                  60
Ser Gly Ser Gly Thr Asp Phe Asn Leu Ser Val Asn Ser Val Glu Thr
 65                 70                  75                  80
Glu Asp Phe Gly Met Tyr Phe Cys Gln Gln Ser Asn Ser Trp Pro Leu
                85                  90                  95
Thr Phe Gly Ala Gly Thr Lys Leu Glu Leu Lys Arg
            100                 105

<210> SEQ ID NO 10
<211> LENGTH: 108
<212> TYPE: PRT
<213> ORGANISM: Artificial sequence
<220> FEATURE:
<223> OTHER INFORMATION: Variable region light chain humanised variant 1
      (VL1)

<400> SEQUENCE: 10

Glu Ile Val Leu Thr Gln Ser Pro Ala Thr Leu Ser Leu Ser Pro Gly
 1               5                  10                  15
Glu Arg Ala Asn Leu Ser Cys Arg Ala Ser Glu Ser Ile Ser Asn Asn
                20                  25                  30
Leu His Trp Tyr Gln Gln Lys Pro His Gln Ala Pro Arg Leu Leu Ile
            35                  40                  45
Lys Tyr Ala Ser Gln Ser Ile Ser Gly Ile Pro Ala Arg Phe Ser Gly
        50                  55                  60
Ser Gly Pro Gly Thr Asp Phe Asn Leu Thr Ile Ser Ser Val Glu Pro
 65                 70                  75                  80
Glu Asp Phe Ala Val Tyr Tyr Cys Gln Gln Ser Asn Ser Trp Pro Leu
                85                  90                  95
Thr Phe Gly Gly Gly Thr Lys Leu Glu Ile Lys Arg
```

100             105

<210> SEQ ID NO 11
<211> LENGTH: 108
<212> TYPE: PRT
<213> ORGANISM: Artificial sequence
<220> FEATURE:
<223> OTHER INFORMATION: Variable region light chain humanised variant 2
      (VL2)

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Pro Gly Thr Asp Phe Thr Leu Thr Ile Ser Ser Val Glu Pro
65                  70                  75                  80

Glu Asp Phe Ala Val Tyr Tyr Cys Gln Gln Ser Asn Ser Trp Pro Leu
                85                  90                  95

Thr Phe Gly Gly Gly Thr Lys Leu Glu Ile Lys Arg
            100                 105

<210> SEQ ID NO 12
<211> LENGTH: 108
<212> TYPE: PRT
<213> ORGANISM: Artificial sequence
<220> FEATURE:
<223> OTHER INFORMATION: Variable region light chain humanised variant 3
      (VL3)

<400> SEQUENCE: 12

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Leu
                85                  90                  95

Thr Phe Gly Gly Gly Thr Lys Leu Glu Ile Lys Arg
            100                 105

<210> SEQ ID NO 13
<211> LENGTH: 108
<212> TYPE: PRT
<213> ORGANISM: Artificial sequence
<220> FEATURE:
<223> OTHER INFORMATION: Variable region light chain humanised variant 4
      (VL4)

<400> SEQUENCE: 13

Glu Ile Val Leu Thr Gln Ser Pro Asp Phe Gln Ser Val Thr Pro Lys
1               5                   10                  15

```
Glu Lys Val Asn Ile Thr Cys Arg Ala Ser Glu Ser Ile Ser Asn Asn
            20                  25                  30

Leu His Trp Tyr Gln Gln Lys Pro His Gln Ser Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Asp Phe Asn Leu Thr Ile Asn Ser Val Glu Ala
65                  70                  75                  80

Glu Asp Ala Ala Thr Tyr Tyr Cys Gln Gln Ser Asn Ser Trp Pro Leu
                85                  90                  95

Thr Phe Gly Gly Gly Thr Lys Leu Glu Ile Lys Arg
                100                 105

<210> SEQ ID NO 14
<211> LENGTH: 108
<212> TYPE: PRT
<213> ORGANISM: Artificial sequence
<220> FEATURE:
<223> OTHER INFORMATION: Variable region light chain humanised variant 5
      (VL5)

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Leu
                85                  90                  95

Thr Phe Gly Gln Gly Thr Lys Val Glu Ile Lys Arg
                100                 105

<210> SEQ ID NO 15
<211> LENGTH: 108
<212> TYPE: PRT
<213> ORGANISM: Artificial sequence
<220> FEATURE:
<223> OTHER INFORMATION: Variable region light chain humanised variant 6
      (VL6)

<400> SEQUENCE: 15

Glu Ile Val Leu Thr Gln Ser Pro Ser Thr Leu Ser Ala Ser Val Gly
1               5                   10                  15

Asp Arg Val Asn Ile Thr Cys Arg Ala Ser Glu Ser Ile Ser Asn Asn
            20                  25                  30

Leu His Trp Tyr Gln Gln Lys Pro His Lys Ala Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Glu Phe Asn Leu Thr Ile Ser Ser Val Gln Pro
65                  70                  75                  80

Asp Asp Phe Ala Thr Tyr Tyr Cys Gln Gln Ser Asn Ser Trp Pro Leu
                85                  90                  95
```

```
Thr Phe Gly Gln Gly Thr Lys Val Glu Ile Lys Arg
            100                 105
```

<210> SEQ ID NO 16
<211> LENGTH: 108
<212> TYPE: PRT
<213> ORGANISM: Artificial sequence
<220> FEATURE:
<223> OTHER INFORMATION: Variable region light chain humanised variant 7
      (VL7)

<400> SEQUENCE: 16

```
Asp Ile Val Leu Thr Gln Ser Pro Ala Thr Leu Ser Leu Ser Pro Gly
1               5                   10                  15

Glu Arg Ala Asn Leu Ser Cys Arg Ala Ser Glu Ser Ile Ser Asn Asn
            20                  25                  30

Leu His Trp Tyr Gln Gln Lys Pro His Gln Ala Pro Arg Leu Leu Ile
        35                  40                  45

Tyr Tyr Ala Ser Gln Ser Ile Ser Gly Val Pro Ala Arg Phe Ser Gly
    50                  55                  60

Ser Gly Ser Gly Thr Asp Phe Asn Leu Thr Ile Ser Ser Val Glu Pro
65                  70                  75                  80

Glu Asp Phe Ala Val Tyr Tyr Cys Gln Gln Ser Asn Ser Trp Pro Leu
                85                  90                  95

Thr Phe Gly Gln Gly Thr Lys Val Glu Ile Lys Arg
            100                 105
```

<210> SEQ ID NO 17
<211> LENGTH: 108
<212> TYPE: PRT
<213> ORGANISM: Artificial sequence
<220> FEATURE:
<223> OTHER INFORMATION: Variable region light chain humanised variant 8
      (VL8)

<400> SEQUENCE: 17

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Ile Ser Asn Asn
            20                  25                  30

Leu His Trp Tyr Gln Gln Lys Pro His Gln Ala Pro Arg Leu Leu Ile
        35                  40                  45

Tyr Tyr Ala Ser Gln Ser Ile Ser Gly Val Pro Ala Arg Phe Ser Gly
    50                  55                  60

Ser Gly Ser Gly Thr Asp Phe Thr Leu Thr Ile Ser Ser Val Glu Pro
65                  70                  75                  80

Glu Asp Phe Ala Val Tyr Tyr Cys Gln Gln Ser Asn Ser Trp Pro Leu
                85                  90                  95

Thr Phe Gly Gln Gly Thr Lys Val Glu Ile Lys Arg
            100                 105
```

<210> SEQ ID NO 18
<211> LENGTH: 5
<212> TYPE: PRT
<213> ORGANISM: Mouse

<400> SEQUENCE: 18

```
Ser Tyr Trp Met Asn
1               5
```

```
<210> SEQ ID NO 19
<211> LENGTH: 17
<212> TYPE: PRT
<213> ORGANISM: Mouse

<400> SEQUENCE: 19

Met Ile His Pro Ser Asp Ser Glu Thr Ile Leu Asn Gln Lys Phe Lys
1               5                   10                  15

Asp

<210> SEQ ID NO 20
<211> LENGTH: 8
<212> TYPE: PRT
<213> ORGANISM: Mouse

<400> SEQUENCE: 20

Trp Ser Ala Lys Arg Gly Asp Phe
1               5

<210> SEQ ID NO 21
<211> LENGTH: 11
<212> TYPE: PRT
<213> ORGANISM: Mouse

<400> SEQUENCE: 21

Arg Ala Ser Glu Ser Ile Ser Asn Asn Leu His
1               5                   10

<210> SEQ ID NO 22
<211> LENGTH: 7
<212> TYPE: PRT
<213> ORGANISM: Mouse

<400> SEQUENCE: 22

Tyr Ala Ser Gln Ser Ile Ser
1               5

<210> SEQ ID NO 23
<211> LENGTH: 9
<212> TYPE: PRT
<213> ORGANISM: Mouse

<400> SEQUENCE: 23

Gln Gln Ser Asn Ser Trp Pro Leu Thr
1               5

<210> SEQ ID NO 24
<211> LENGTH: 30
<212> TYPE: DNA
<213> ORGANISM: Artificial sequence
<220> FEATURE:
<223> OTHER INFORMATION: MK Sense primer

<400> SEQUENCE: 24
gcggaattca tgcagcaccg aggcttcctc                                    30

<210> SEQ ID NO 25
<211> LENGTH: 30
<212> TYPE: DNA
<213> ORGANISM: Artificial sequence
```

```
<220> FEATURE:
<223> OTHER INFORMATION: MK Antisense primer

<400> SEQUENCE: 25
gcggaattcc tagtcctttc ccttcccttt                                30
```

MIDKINE ANTIBODY

CROSS-REFERENCE TO RELATED APPLICATIONS

This application claims priority to and the benefit of Australian Provisional Patent Application No. 2014904102, filed Oct. 14, 2014, and International Patent Application No. PCT/AU2015/050629, filed on Oct. 14, 2015, the disclosure of which is incorporated herein by reference in its entirety.

FIELD OF THE INVENTION

The present disclosure is directed to isolated or recombinant proteins, such as antibodies, which bind to, and inhibit or reduce the function of, midkine (hereinafter, referred to as "MK") and their use as therapeutic and/or diagnostic agents for midkine-related disorders. The present disclosure is also related to nucleic acid sequences which encode said proteins and their expression in recombinant host cells. In particular, the present disclosure is directed towards humanized antibodies derived from murine antibody IP14 which specifically bind to human MK.

BACKGROUND OF THE INVENTION

Midkine (hereinafter, referred to as "MK") is a growth/differentiation factor found as a product of a gene transiently expressed in the stage of retinoic acid-induced differentiation of embryonal carcinoma (EC) cells and is a polypeptide of 13 kDa in molecular weight rich in basic amino acids and cysteine (Kadomatsu. et al. (1988) *Biochem. Biophys. Res. Commun.*, 1511312-1318; Tomokura et al. (1999) *J. Biol. Chem.* 265:10765-10770).

MK is known to have various biological activities. For example, it is known that MK expression is increased in human cancer cells. This increase in expression has been confirmed in various cancers such as esophageal cancer, thyroid cancer, urinary bladder cancer, colon cancer, stomach cancer, pancreatic cancer, thoracic cancer, liver cancer, lung cancer, breast cancer, neuroblastoma, glioblastoma, uterine cancer, ovarian cancer, and Wilms tumor (Muramatsu (2002) *J. Biochem.* 132:359-371). Moreover, MK is thought to promote the survival and migration of cancer cells, promote angiogenesis, and contribute to cancer progression.

MK is also known to play a central role in the stage of inflammation formation. For example, it is known that neointimal formation after vascular injury and nephritis onset during ischemic injury are suppressed in knockout mice deficient in MK genes. Moreover, it is also known that rheumatism models and postoperative adhesion are significantly suppressed in such knockout mice (WO2000/10608; WO2004/078210). Thus, MK is known to participate in inflammatory diseases such as arthritis, autoimmune disease, rheumatic arthritis (rheumatoid arthritis (RA) or osteoarthritis (OA)), multiple sclerosis, postoperative adhesion, inflammatory bowel disease, psoriasis, lupus, asthma, and neutrophil dysfunction. Furthermore, MK is known to promote the movement (migration) of inflammatory cells such as macrophages or neutrophils. Since this movement is necessary for the establishment of inflammation, it is thought that deficiency of MK probably prevents diseases based on inflammation (WO1999/03493).

The three-dimensional structure of MK has been determined by NMR and reported (Iwasaki et al. (1997) *EMBO J.* 16, p. 6936-6946). MK is composed of: an N-terminal fragment (hereinafter, referred to as an "N-fragment") consisting of amino acid residues 1 to 52; a C-terminal fragment (hereinafter, referred to as a "C-fragment") consisting of amino acid residues 62 to 121; and a loop region (amino acid residues 53 to 61) (hereinafter, referred to as a "loop") that links these fragments.

Each of the N- and C-fragments is mainly composed of: a portion having a three-dimensional structure consisting of three antiparallel [beta]-sheets (hereinafter, referred to as a "domain"; the domain (consisting of amino acid residues 15 to 52) in the N-fragment is referred to as an "N-domain", and the domain (consisting of amino acid residues 62 to 104) in the C-fragment is referred to as a "C-domain"); and a terminally located portion devoid of the domain that does not assume a particular three-dimensional structure (hereinafter, referred to as a "tail"; the tail (consisting of amino acid residues 1 to 14) in the N-fragment is referred to as an "N-tail", and the tail (consisting of amino acid residues 105 to 121) in the C-fragment is referred to as a "C-tail"). Basic amino acids on the C-domain surface form two clusters: a cluster consisting of lysine 79, arginine 81, and lysine 102 (cluster 1) and a cluster consisting of lysine 86, lysine 87, and arginine 89 (cluster II). Both the clusters are known to participate in heparin-binding ability.

The C-terminally located domain is usually responsible for MK activity (Kojima et al. (1995) *Biochem Biophys. Res. Comm.* 206:468-473; Muramatsu et al. (1994) *Biochem Biophys. Res. Comm.* 203:1131-1139; Matsui et al. (2010) *Int. Arch Medicine* 3:12). Development of anti-MK antibodies has therefore focused on antibodies which are directed against the C-domain.

Whilst anti-MK antibodies against the C-domain of MK are known e.g., as disclosed in WO2008/059616, there is a need for improved antibodies targeting MK, such as the C-domain of MK, with improved ability to inhibit or reduce MK activity or function in humans.

SUMMARY

Humanised antibodies against the C-domain of human midkine have been prepared and it has been unexpectedly shown that these humanised antibodies inhibit the midkine-mediated cell migration to a substantially greater extent than the corresponding murine IP14 precursor antibody. For example, it has been shown that exemplary humanised anti-midkine antibodies of the disclosure inhibit the cell migration function of midkine in a UMR106 cell migration inhibition model to a substantially greater extent than the corresponding murine precursor antibody from which they derive.

Accordingly, the present disclosure provides a substantially purified and/or recombinant antibody comprising:
(i) an immunoglobulin heavy chain comprising a variable region comprising an amino acid sequence having 95% identity to a sequence set forth in SEQ ID NO: 8, wherein residue at position 16 is G or H, residue at position 43 is Q or K, residue at positions 71 and 78 is S or T, and residue at position 75 is S or A; and/or
(ii) an immunoglobulin light chain comprising a variable region comprising an amino acid sequence having 95% identity to a sequence set forth in SEQ ID NO: 17,
wherein the antibody binds human midkine (huMK) protein.

In one example, the antibody comprises:
(i) an immunoglobulin heavy chain comprising a variable region comprising an amino acid sequence having 95% identity to a sequence set forth in SEQ ID NO: 8, wherein residue at position 16 is G or H, residue at position 43 is Q or K, residue at positions 71 and 78 is S or T, and residue at position 75 is S or A; and
(ii) an immunoglobulin light chain comprising a variable region comprising an amino acid sequence having 95% identity to a sequence set forth in SEQ ID NO: 17.

In one example, the antibody comprises:
(i) an immunoglobulin heavy chain comprising a variable region comprising an amino acid sequence having 95% identity to a sequence set forth in SEQ ID NO: 8, wherein residue at position 16 is G or H, residue at position 43 is Q or K, residue at positions 71 and 78 is S or T, and residue at position 75 is S or A; and
(ii) an immunoglobulin light chain comprising a variable region comprising an amino acid sequence having 95% identity to a sequence set forth in SEQ ID NO: 17.

For example, the antibody may comprise:
(i) an immunoglobulin heavy chain comprises a variable region comprising an amino acid sequence set forth in SEQ ID NO: 6; and
(ii) an immunoglobulin light chain comprises a variable region comprising an amino acid sequence set forth in SEQ ID NO: 17.

For example, the antibody may comprise
(i) an immunoglobulin heavy chain comprises a variable region comprising an amino acid sequence set forth in SEQ ID NO: 7; and
(ii) an immunoglobulin light chain comprises a variable region comprising an amino acid sequence set forth in SEQ ID NO: 17.

In another example, the present disclosure also provides a substantially purified and/or recombinant antibody comprising:
(i) an immunoglobulin heavy chain comprising a variable region comprising an amino acid sequence having 95% identity to a sequence set forth in SEQ ID NO: 7; and
(ii) an immunoglobulin light chain comprising a variable region comprising an amino acid sequence having 95% identity to a sequence set forth in SEQ ID NO: 12,
wherein the antibody binds human midkine (huMK) protein.

For example, the antibody comprises:
(i) an immunoglobulin heavy chain comprising a variable region comprising an amino acid sequence having 95% identity to a sequence set forth in SEQ ID NO: 7; and
(ii) an immunoglobulin light chain comprising a variable region comprising an amino acid sequence having 95% identity to a sequence set forth in SEQ ID NO: 12,
wherein the antibody binds human midkine (huMK) protein.

For example, the antibody comprises:
(i) an immunoglobulin heavy chain comprising a variable region comprising an amino acid sequence having a sequence set forth in SEQ ID NO: 7; and
(ii) an immunoglobulin light chain comprising a variable region comprising an amino acid sequence having a sequence set forth in SEQ ID NO: 12,
wherein the antibody binds human midkine (huMK) protein.

The antibody can be of any suitable structure known in the art. Examples include, but are not limited to, a four-polypeptide chain structure consisting of two heavy and two light chains, a single chain antibody, diabody, triabody or tetrabody, as well as antibody fragments such as, but not limited to, a Fab fragment or single domain antibody which bind huMK.

In a preferred example, the antibody will have a binding affinity for huMK which is greater than the binding affinity of the corresponding murine IP14 precursor antibody for huMK under equivalent conditions, wherein the murine IP14 precursor antibody comprises (i) an immunoglobulin heavy chain comprising a variable region comprising an amino acid sequence set forth in SEQ ID NO:1 and (ii) an immunoglobulin light chain comprising a variable region comprising an amino acid sequence set forth in SEQ ID NO:9.

The present disclosure also provides a conjugate comprising an antibody of the disclosure and a compound which is directly or indirectly bound to the antibody.

In one example, the compound is selected from the group consisting of a radioisotope, a detectable label, a therapeutic agent, a colloid, a toxin, a nucleic acid, a peptide, a protein, a compound that increases the half-life of the antibody in a subject and mixtures thereof.

For example, the therapeutic agent may be selected from the group consisting of: a cytotoxin, a radioisotope, an immunomodulatory agent, an anti-angiogenic agent, a toxin, an anti-proliferative agent, a pro-apoptotic agent, a chemotherapeutic agent e.g., carboplatin, and a therapeutic nucleic acid.

For example, the detectable label may be selected from the group consisting of: a radiolabel, a fluorescent label, an enzymatic label and an imaging agent.

In one example, the compound is indirectly bound to the antibody via a linker.

The present disclosure also provides an isolated and/or recombinant polynucleotide encoding an antibody of the disclosure.

The present disclosure also provides a vector comprising the polynucleotide of the disclosure. Preferably, the vector is an expression vector. More preferably, the polynucleotide is operably-linked to a promoter.

The present disclosure also provides a host cell comprising a polynucleotide of the disclosure and/or a vector of the disclosure. The host cell can be any cell type such as a bacterial, yeast, plant or animal cell.

The present disclosure also provides a pharmaceutical composition comprising an antibody, or a conjugate of the disclosure, and a pharmaceutically acceptable carrier.

In one example, the pharmaceutical composition may comprise a further therapeutic agent selected from the group consisting of: a cytotoxin, a radioisotope, an immunomodulatory agent, an anti-angiogenic agent, a toxin, an anti-proliferative agent, a pro-apoptotic agent, a chemotherapeutic agent e.g., carboplatin, and a therapeutic nucleic acid.

The present disclosure also provides a method for producing an antibody of the disclosure, said method comprising:
(i) culturing a host cell of the disclosure for a time and under conditions sufficient for the host cell to produce the antibody; and optionally
(ii) recovering the antibody produced at (i) from the cell culture.

Preferably, the method comprises recovering the antibody from the host cell culture. More preferably, the method comprises purifying the recovered antibody.

The present disclosure also provides a method for inhibiting an interaction between human midkine and a ligand thereof in a cell, said method comprising exposing the cell to an antibody of the disclosure, a conjugate of the disclosure or pharmaceutical composition of the disclosure.

The present disclosure also provides a method for inhibiting human midkine activity in a cell, said method comprising exposing the cell to an antibody of the disclosure or a conjugate of the disclosure or a pharmaceutical composition of the disclosure.

The present disclosure also provides a method for treating or preventing a midkine-related disease or disorder in a subject in need thereof, said method comprising administering to the subject an antibody of the disclosure or a conjugate of the disclosure or a pharmaceutical composition of the disclosure.

Examples of midkine-related diseases or disorders that can be treated or prevented include, but are not limited to, autoimmune diseases, cancer, inflammatory diseases or multiple sclerosis. Preferably, the midkine-related disease or disorder is cancer. In another preferred embodiment, the midkine-related disease or disorder is an inflammatory disease.

The method of the disclosure can be performed in combination with other known therapies. Thus, an embodiment of the method further comprises administering at least one other compound for treating or preventing the midkine-related disease or disorder. Such other therapies can be provided concurrently or sequentially.

In an example where the midkine-related disease or disorder to be treated is cancer, the method further comprises administration of a chemotherapeutic agent to the subject. Preferably the chemotherapeutic agent is carboplatin.

The present disclosure also provides a method of detecting the presence or absence of human midkine in a sample, said method comprising:
(i) contacting the sample with an antibody the disclosure and/or a conjugate of the disclosure; and
(ii) analysing the sample for binding between human midkine and the antibody or conjugate.

Methods for detecting binding between an antibody and a binding partner are well known in the art. Accordingly, it will be understood that the step of analysing the sample for binding between human midkine and the antibody or conjugate may be performed by any means known in the art.

Examples of suitable samples which can be tested include, but are not necessarily limited to, blood, serum, plasma, as well as cell or tissue biopsies.

The present disclosure also provides a method for diagnosing a midkine-related disease or disorder in a subject, said method comprising:
(i) performing a method of detecting the presence or absence of human midkine of the disclosure on a sample obtained from the subject to determine the presence or absence of human midkine in the sample; and
(ii) diagnosing the midkine-related disease or disorder based on the presence or absence of human midkine in the sample.

Thus, the method may be performed in vitro.

Examples of suitable samples which can be tested include, but are not necessarily limited to, blood, serum, plasma, as well as cell or tissue biopsies. Preferably, the sample is a histological specimen, subfraction of tissue or fluid obtained from the subject.

Examples of midkine-related diseases or disorders that can be diagnosed include, but are not limited to, autoimmune diseases, cancer, inflammatory diseases or multiple sclerosis. Preferably, the midkine-related disease or disorder is diagnosed is cancer. In another preferred embodiment, the midkine-related disease or disorder in an inflammatory disease.

Also provided is the use of an antibody of the disclosure and/or a conjugate of the disclosure and/or a polynucleotide of the disclosure and/or a vector of the disclosure and/or a host cell of the disclosure and/or a pharmaceutical composition of the disclosure in the preparation of a medicament for treatment or prevention of a midkine-related disease or disorder selected from an autoimmune disease, cancer, an inflammatory disease or multiple sclerosis in a subject in need thereof.

Preferably, the medicament is for treatment of cancer. In another preferred embodiment, the medicament is for treatment of an inflammatory disease.

The medicament may also comprise other compounds known for treatment or prevention of the midkine-related disease or disorder. Thus, in one embodiment the medicament further comprises at least one other compound for treating or preventing the midkine-related disease or disorder. For example, the medicament may further comprises a chemotherapeutic agent. Preferably, the chemotherapeutic agent is carboplatin.

Also provided is the use of an antibody of the disclosure and/or a conjugate of the disclosure and/or a polynucleotide of the disclosure and/or a vector of the disclosure and/or a host cell of the disclosure and/or a pharmaceutical composition of the disclosure in the preparation of a diagnostic reagent for diagnosing a midkine-related disease or disorder selected from an autoimmune disease, cancer, an inflammatory disease or multiple sclerosis in a subject in need thereof.

Preferably, the diagnostic reagent is for diagnosing cancer. In another preferred embodiment, the diagnostic reagent is for diagnosing an inflammatory disease.

Also provided is the use of an antibody of the disclosure and/or a conjugate of the disclosure and/or a pharmaceutical composition of the disclosure to treat or prevent a midkine-related disease or disorder selected from an autoimmune disease, cancer, an inflammatory disease or multiple sclerosis in a subject in need thereof. Preferably, the midkine-related disease or disorder is cancer. In another preferred embodiment, the midkine-related disease or disorder is an inflammatory disease.

Also provided is the use of an antibody of the disclosure and/or a conjugate of the disclosure to diagnose a midkine-related disease or disorder selected from an autoimmune disease, cancer, an inflammatory disease or multiple sclerosis in a subject. Preferably, the midkine-related disease or disorder is cancer. In another preferred embodiment, the midkine-related disease or disorder is an inflammatory disease.

The present disclosure also provides a kit comprising:
(i) a first container comprising an antibody of the disclosure and/or a conjugate of the disclosure and/or a pharmaceutical composition of the disclosure; and
(ii) a second container comprising a compound selected from the group consisting of a radioisotope, a detectable label, a therapeutic agent, a colloid, a toxin, a nucleic acid, a peptide, a protein, a compound that increases the half-life of the antibody in a subject and mixtures thereof.

For example, the therapeutic agent may be selected from the group consisting of: a cytotoxin, a radioisotope, an immunomodulatory agent, an anti-angiogenic agent, a toxin, an anti-proliferative agent, a pro-apoptotic agent, a chemotherapeutic agent, and a therapeutic nucleic acid.

For example, the detectable label may selected from the group consisting of: a radiolabel, a fluorescent label, an enzymatic label and an imaging agent.

As will be apparent, preferred features and characteristics of one aspect of the disclosure are applicable to many other aspects of the disclosure.

The invention is hereinafter described by way of the following non-limiting Examples and with reference to the accompanying figures.

BRIEF DESCRIPTION OF THE ACCOMPANYING DRAWINGS

FIG. 1. Z-scores for (i) mIP14 heavy chain variable region humanization variants and (ii) mIP14 light chain variable region humanization variants.

Figure 2:
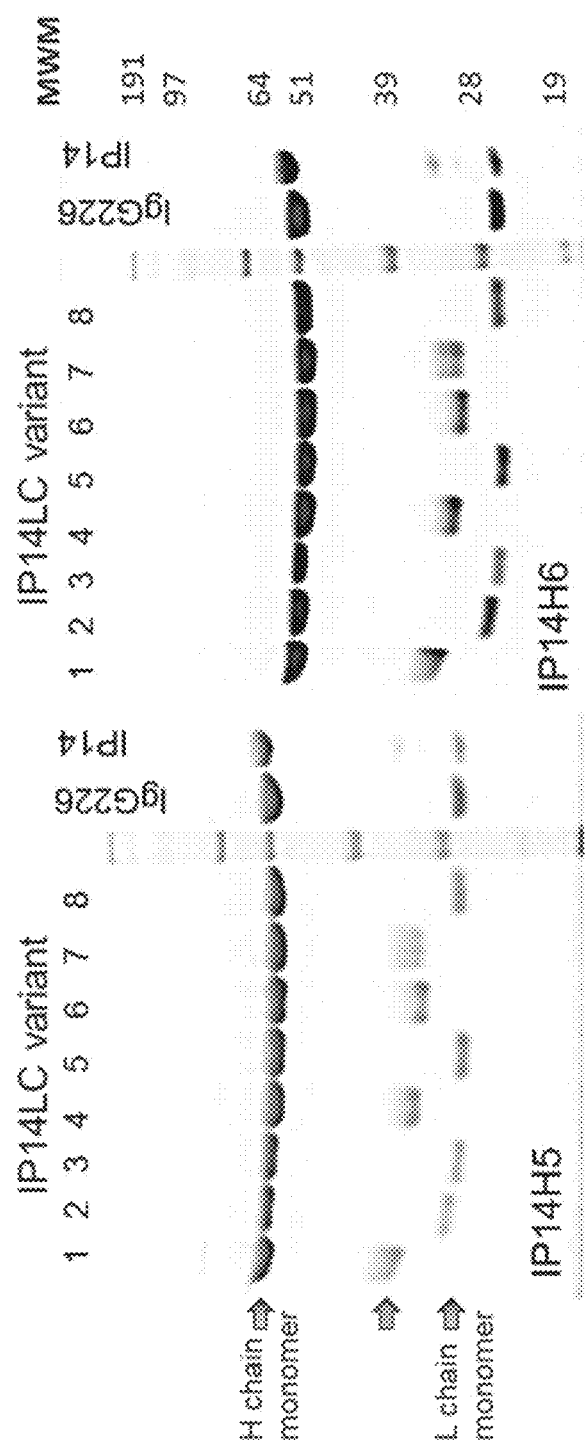

FIG. 2. Reducing SDS-PAGE for candidate humanized IP14 antibodies having heavy chain variant Hv5 or Hv6. The humanised IP14 antibodies comprising a humanised light chain variant selected from Lv1, Lv4, Lv6 and Lv7 show N-glycolsylation on the light chains.

Figure 3:
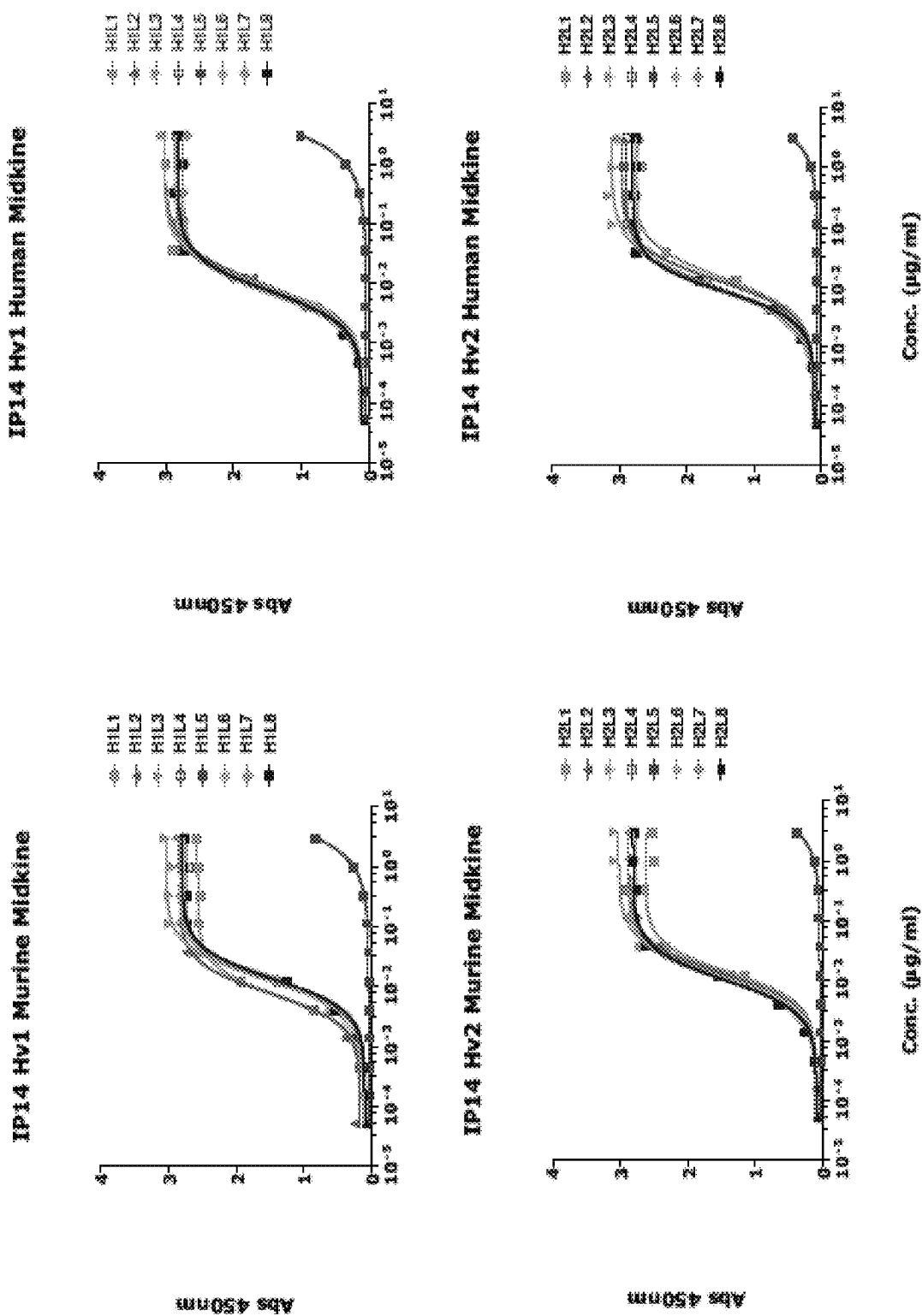
Figure 3:
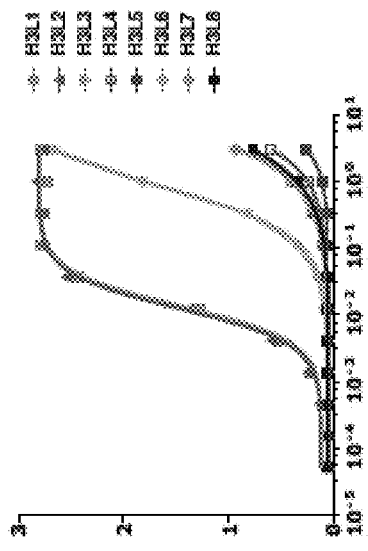
Figure 3:
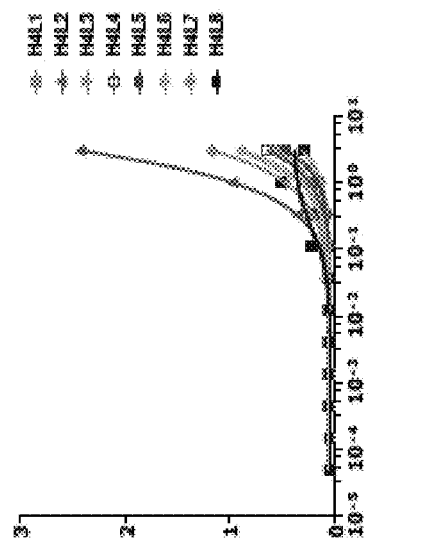
Figure 3:
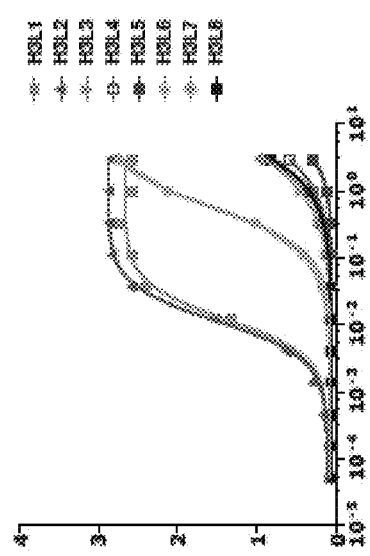
Figure 3:
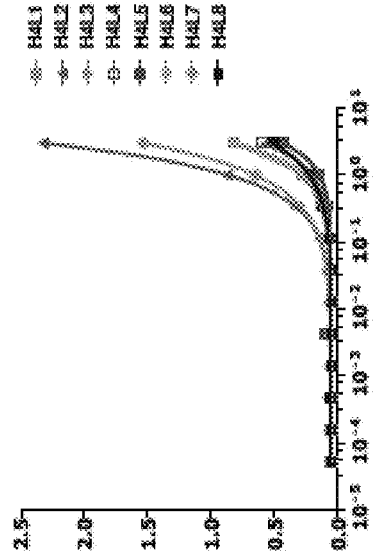
Figure 3:
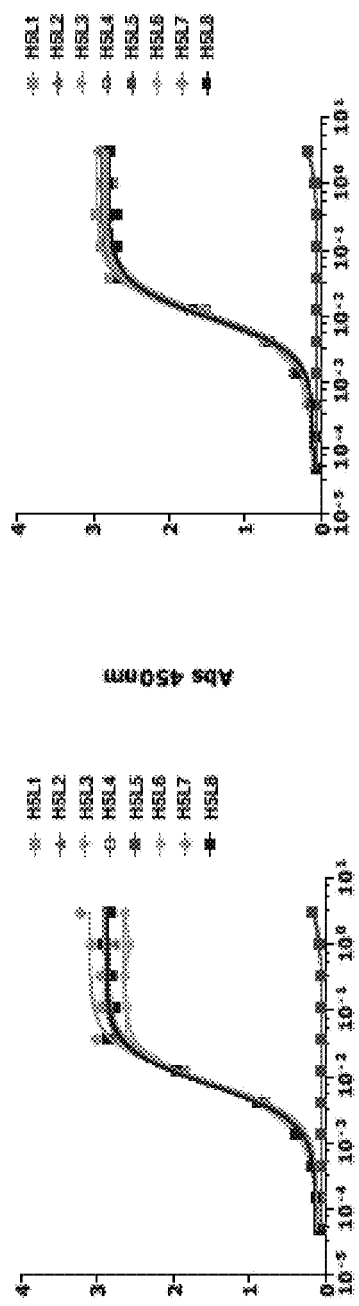
Figure 3:
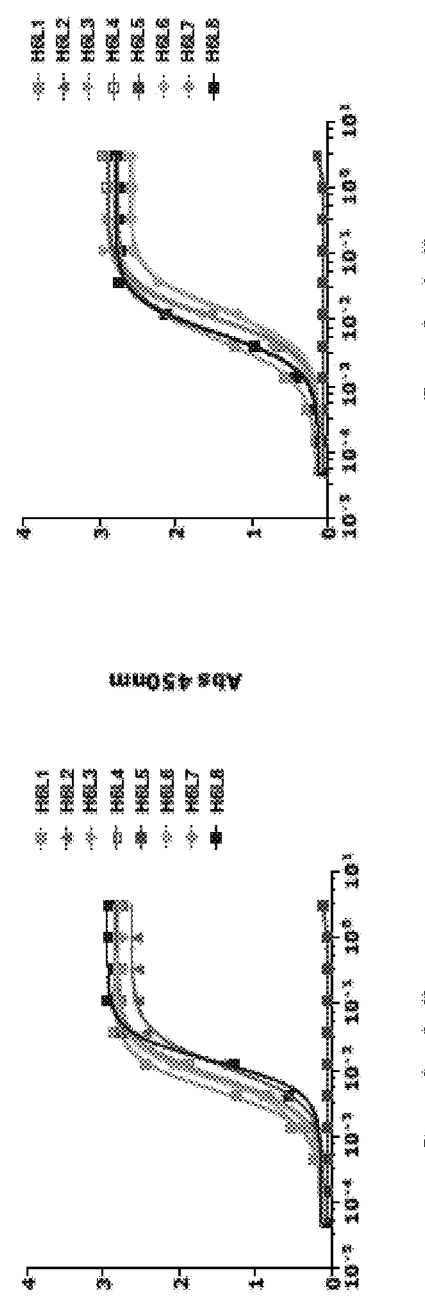
Figure 3:
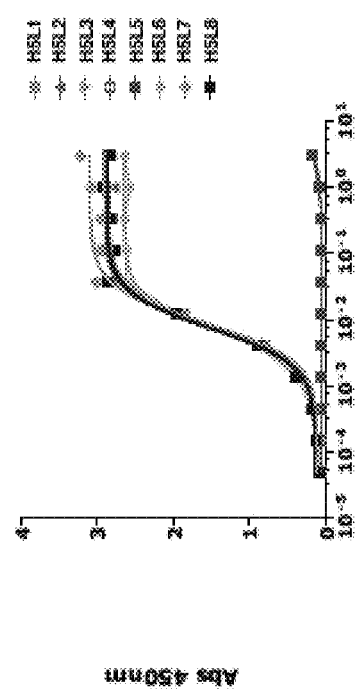
Figure 3:
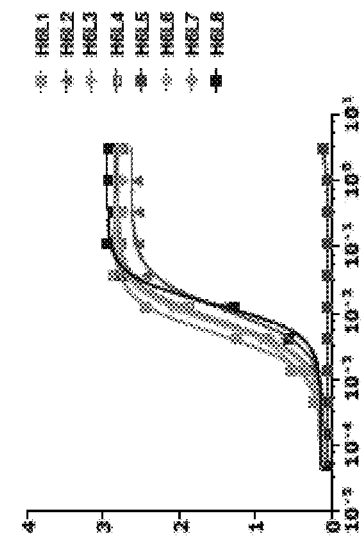

FIG. 3. ELISA binding affinity data for the humanised IP14 antibodies to huMK and muMK.

Figure 4:
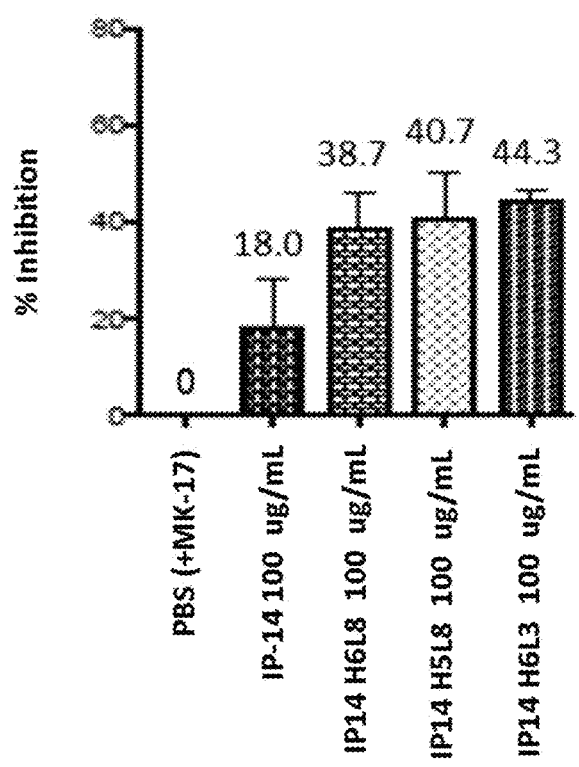

FIG. 4. Percentage inhibition of migration of UMR106 cell to human midkine protein in the presence of mAb IP14, and humanized IP14 antibodies designated IP14-H6L8, IP14-H5L8 and IP14-H6L3 (each at 100 mg/mL).

KEY TO THE SEQUENCE LISTING

SEQ ID NO:1—Murine IP14 variable heavy chain protein sequence.
SEQ ID NO:2—Humanised IP14 variable heavy chain variant Hv1 protein sequence.
SEQ ID NO:3—Humanised IP14 variable heavy chain variant Hv2 protein sequence.
SEQ ID NO:4—Humanised IP14 variable heavy chain variant Hv3 protein sequence.
SEQ ID NO:5—Humanised IP14 variable heavy chain variant Hv4 protein sequence.
SEQ ID NO:6—Humanised IP14 variable heavy chain variant Hv5 protein sequence.
SEQ ID NO:7—Humanised IP14 variable heavy chain variant Hv6 protein sequence.
SEQ ID NO:8—Humanised IP14 variable heavy chain consensus variant Hv5/6 protein sequence.
SEQ ID NO:9—Murine IP14 variable light chain protein sequence.
SEQ ID NO:10—Humanised IP14 variable light chain variant Lv1 protein sequence.
SEQ ID NO:11—Humanised IP14 variable light chain variant Lv2 protein sequence.
SEQ ID NO:12—Humanised IP14 variable light chain variant Lv3 protein sequence.
SEQ ID NO:13—Humanised IP14 variable light chain variant Lv4 protein sequence.
SEQ ID NO:14—Humanised IP14 variable light chain variant Lv5 protein sequence.
SEQ ID NO:15—Humanised IP14 variable light chain variant Lv6 protein sequence.
SEQ ID NO:16—Humanised IP14 variable light chain variant Lv7 protein sequence.
SEQ ID NO:17—Humanised IP14 variable light chain variant Lv8 protein sequence.
SEQ ID NO:18—Murine IP14 variable heavy chain CDR1 protein sequence.
SEQ ID NO:19—Murine IP14 variable heavy chain CDR2 protein sequence.
SEQ ID NO:20—Murine IP14 variable heavy chain CDR3 protein sequence.
SEQ ID NO:21—Murine IP14 variable light chain CDR1 protein sequence.
SEQ ID NO:22—Murine IP14 variable light chain CDR2 protein sequence.
SEQ ID NO:23—Murine IP14 variable light chain CDR3 protein sequence.
SEQ ID NO:24—Human midkine sense primer sequence.
SEQ ID NO:25—Human midkine antisense primer sequence.

DETAILED DESCRIPTION OF THE INVENTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Selected Definitions

The skilled artisan will be aware that an "antibody" is generally considered to be a protein that comprises a variable region made up of a plurality of immunoglobulin chains, e.g., a polypeptide comprising a $V_L$ and a polypeptide comprising a $V_H$. An antibody also generally comprises constant domains, some of which can be arranged into a constant region or constant fragment or fragment crystallizable (Fc). A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, de-immunized antibodies, non-depleting antibodies, non-activating antibodies, primatized antibodies, human antibodies and chimeric antibodies. As used herein, the term "antibody" is also intended to include formats other than full-length, intact or whole antibody molecules, such as Fab, F(ab')2, and Fv which are capable of binding the epitopic determinant. These formats may be referred to as antibody "fragments". These antibody formats retain some ability to selectively bind to human midkine, examples of which include, but are not limited to, the following:

(1) Fab, the fragment which contains a monovalent binding fragment of an antibody molecule and which can be produced by digestion of whole antibody with the enzyme papain to yield an intact light chain and a portion of one heavy chain;

(2) Fab', the fragment of an antibody molecule which can be obtained by treating whole antibody with pepsin, followed by reduction, to yield an intact light chain and a portion of the heavy chain; two Fab' fragments are obtained per antibody molecule:

(3) $(Fab')_2$, the fragment of the antibody that can be obtained by treating whole antibody with the enzyme pepsin without subsequent reduction; $F(ab)_2$ is a dimer of two Fab' fragments held together by two disulfide bonds;

(4) Fv, defined as a genetically engineered fragment containing the variable region of the light chain and the variable region of the heavy chain expressed as two chains;

(5) Single chain antibody ("SCA"), defined as a genetically engineered molecule containing the variable region of the light chain, the variable region of the heavy chain, linked by a suitable polypeptide linker as a genetically fused single chain molecule; such single chain antibodies may be in the form of multimers such as diabodies, triabodies, and tetrabodies etc which may or may not be polyspecific (see, for example, WO 94/07921 and WO 98/44001); and (6) Single domain antibody, typically a variable heavy domain devoid of a light chain.

Accordingly, an antibody in accordance with the present disclosure includes separate heavy chains, light chains, Fab, Fab', F(ab')2, Fc, a variable light domain devoid of any heavy chain, a variable heavy domain devoid of a light chain and Fv. Such fragments can be produced by recombinant DNA techniques, or by enzymatic or chemical separation of intact immunoglobulins.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof. In some cases, the intact antibody may have one or more effector functions.

The antibody disclosed herein may be a humanized antibody. The term "humanized antibody", as used herein, refers to an antibody derived from a non-human antibody, typically murine, that retains or substantially retains the antigen-binding properties of the parent antibody but which is less immunogenic in humans.

The antibody disclosed herein may be a non-depleting antibody. The term "non-depleting antibody", as used herein, refers to an antibody that binds to its target but does not recruit the immune system's effector functions which effect target cell lysis. The immune system's effector functions are dependent on interactions of the Fc-domain with C1q, the first component of the complement cascade, and/or receptors (FcR). Complement-dependent cytotoxicity (CDC) is initiated by multiple Fc-domains interacting with C1q, which can ultimately result in lysis of target cells through the formation of the membrane attack complex (MAC). Additionally, cells of the immune system, such as granulocytes, macrophages, and NK cells, may interact via FcRs with mAbs bound to target cells. Lysis of target cells is triggered via antibody-dependent cell mediated cytotoxicity (ADCC) or phagocytosis. Non-depleting antibodies include antibody fragments without an Fc domain, including for example, monovalent (e.g., Fab, scFv, nanobodies and dAbs), bivalent (e.g., $F(ab')_2$ and diabodies) and multivalent (e.g., triabodies and pentabodies) formats. In addition, non-depleting antibodies include antibodies that have been modified to remove effector functions without impacting pharmokinetics, for example, amino acid residues in the Fc-domain that play a dominant role in interaction with C1q and FcRs could be modified, or the N-linked glycosylation site in the CH2 domain could be removed. As a skilled person is aware, the chances of engineering a non-depleting antibody are linked to the constant region used to produce the antibody. An IgG3 constant region is more likely to produce a depleting antibody than an IgG1 constant region which in turn is more likely to produce a depleting antibody than an IgG2 constant region, whereas an IgG4 constant region will generally mean that the antibody is non-depleting. A skilled person would also understand that modifications to a constant region could convert a depleting antibody into a non-depleting antibody and vice versa.

The antibody disclosed herein may be a non-activating antibody. As used herein, a "non-activating antibody" refers to antibodies that bind cell surface receptors and negate or block the action of endogenous ligands.

As used herein, "variable region" refers to the portions of the light and/or heavy chains of an antibody as defined herein that is capable of specifically binding to an antigen and, for example, includes amino acid sequences of CDRs; i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain. The amino acid positions assigned to CDRs and FRs can be defined according to Kabat (1987 and 1991, supra) or other numbering systems in the performance of methods according to the present disclosure, e.g., the hypervariable loop numbering system of Clothia and Lesk (1987 and/or 1989, supra and/or Al-Lazikani et al., 1997, supra).

As used herein, the term "complementarity determining regions" (syn. CDRs; i.e., CDR1, CDR2, and CDR3) refers to the amino acid residues of an antibody variable domain that form loops between the FRs the sequence of which vary between antibodies. Some or all of the CDRs confer the ability to bind antigen on the antibody. Each variable domain typically has three CDR regions identified as CDR1, CDR2 and CDR3. Each complementarity determining region may comprise amino acid residues from a "complementarity determining region" as defined by Kabat et al., (1991) and/or those residues from a "hypervariable loop" Chothia and Lesk (1987), or any other known numbering technique or combination thereof, including the IMGT numbering system (Le Franc et al., 2003).

"Framework regions" (hereinafter FR) are those variable domain residues other than the CDR residues.

The term "constant region" or "fragment crystalizable" or "Fc" or "Fc region" or "Fc portion" (which can be used interchangeably herein) as used herein, refers to a portion of an antibody comprising at least one constant domain and which is generally (though not necessarily) glycosylated and which is capable of binding to one or more Fc receptors and/or components of the complement cascade. The heavy chain constant region can be selected from any of the five isotypes: α, δ, ε, γ, or μ. Furthermore, heavy chains of various subclasses (such as the IgG subclasses of heavy chains) are responsible for different effector functions and thus, by choosing the desired heavy chain constant region, proteins with desired effector function can be produced. Preferably, the constant regions of the antibodies of the disclosure are derived from human immunoglobulins. Exemplary heavy chain constant regions are gamma 1 (IgG1), gamma 2 (IgG2), gamma 3 (IgG3), gamma 4 (IgG4), or hybrids thereof. The light chain constant region can be of the kappa or lambda type, preferably of the kappa type.

A "constant domain" is a domain in an antibody the sequence of which is highly similar in antibodies/antibodies of the same type, e.g., IgG or IgM or IgE. A constant region of an antibody generally comprises a plurality of constant domains, e.g., the constant region of γ, α and δ heavy chains comprises two constant domains.

As will be appreciated by the person skilled in the art, the term "residue" as used herein refers to an amino acid residue. Thus, the word "residue" may be used interchangeably with the term "amino acid".

The term "recombinant" in the context of an antibody refers to the antibody when produced by a cell, or in a cell-free expression system, in an altered amount or at an altered rate compared to its native state. In one embodiment, the cell is a cell that does not naturally produce the antibody or immunoglobulin chain. However, the cell may be a cell which comprises a non-endogenous gene that causes an altered, preferably increased, amount of the polypeptide to be produced. A recombinant antibody of the disclosure includes polypeptides which have not been separated from other components of the transgenic (recombinant) cell, or cell-free expression system, in which it is produced, and an antibody produced in such cells or cell-free systems which are subsequently purified away from at least some other components.

The antibody disclosed herein may specifically bind to midkine protein (such as human midkine protein). As used herein, the term "specifically binds" shall be taken to mean a protein reacts or associates more frequently, more rapidly, with greater duration and/or with greater affinity with midkine or a specified epitope thereof than it does with alternative antigens or epitopes. As such, "specific binding" does not necessarily require exclusive binding or non-detectable binding of another antigen. The term specifically binds" is used interchangeably with "selectively binds" herein.

By "overlapping" in the context of two epitopes shall be taken to mean that two epitopes share a sufficient number of amino acid residues to permit an antibody that binds to one epitope to competitively inhibit the binding of an antibody that binds to the other epitope. For example, the two epitopes share at least 1 or 2 or 3 or 4 or 5 or 6 or more amino acids.

Reference herein to "monoclonal antibody IP-14", "IP-14" or "murine IP-14" is a reference to the monoclonal antibody which has a variable heavy chain sequence as shown in SEQ ID NO:1 and a variable light chain sequence as shown in SEQ ID NO: 9. mAb IP14 is the same antibody as designated CSM-4 in WO2008/059616.

As used herein, the terms "treating", "treat" or "treatment" and variations thereof, refer to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease (e.g., cancer) are mitigated or eliminated.

As used herein, the terms "preventing", "prevent" or "prevention" or variations thereof, refers to the provision of prophylaxis with respect to occurrence or recurrence of a disease in an individual. An individual may be predisposed to or at risk of developing the disease or disease relapse but has not yet been diagnosed with the disease or the relapse. The term prevention does not require absolute prevention but includes inhibiting the progression of the disease to some extent.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is meant an amount necessary to effect treatment of a disease or condition as hereinbefore described. The effective amount may vary according to the disease or condition to be treated and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner. The effective amount can be administered in a single dose or in a dose repeated once or several times over a treatment period.

A "therapeutically effective amount" is at least the minimum concentration required to effect a measurable improvement of a particular disease (e.g., cancer). A therapeutically effective amount herein may vary according to factors such as the disease state, age, sex, and weight of the patient, and the ability of the protein to elicit a desired response in the individual. A therapeutically effective amount is also one in which any toxic or detrimental effects of the protein are outweighed by the therapeutically beneficial effects.

A "prophylactically effective amount" refers to an amount effective, at the dosages and for periods of time necessary, to achieve the desired prophylactic result. Typically but not necessarily, since a prophylactic dose is used in mammals prior to or at an earlier stage of disease, a prophylactically effective amount may be less than a therapeutically effective amount.

The term "effective concentration 50%" (abbreviated as "$EC_{50}$") represents the concentration of an antibody of the disclosure that is required for 50% of a given effect of the molecule the antibody targets (e.g. inhibiting/displacing binding of human midkine to a target thereof). It will be understood by one in the art that a lower $EC_{50}$ value corresponds to a more potent antibody.

The "mammal" treated according to the present disclosure may be a primate, livestock (e.g. sheep, horses, cattle, pigs, donkeys), companion animal (e.g. pets such as dogs and cats), laboratory test animal (e.g. mice, rabbits, rats, guinea pigs), performance animal (e.g. racehorses, camels, greyhounds) or captive wild animal. In one example, the mammal is a human.

Anti-midkine Antibodies

The present disclosure provides antibodies that are structurally and/or functionally related to murine anti-midkine antibody IP-14 (described as CSM-4 in WO2008/059616), e.g., humanised antibodies, in which an immunoglobulin heavy chain comprises a variable region sequence which exhibits a degree of identity to SEQ ID NO:1 and an immunoglobulin light chain comprises a variable region sequence which exhibits a degree of identity to SEQ ID NO:9. Preferably, the antibodies bind human midkine (huMK) protein. Preferably, the antibodies recognize an epitope located at amino acid residues 62 to 104 of huMK.

In one example, the antibodies comprise an immunoglobulin heavy chain comprising a variable region comprising an amino acid sequence having at least 95% identity to a sequence set forth in any one of SEQ ID NOs: 2-8. Preferably, the immunoglobulin heavy chain comprises a variable region comprising 3 CDRs of murine IP14 set forth in SEQ ID NOs: 18-20. For example, the antibodies may comprise an immunoglobulin heavy chain comprising a variable region comprising an amino acid sequence set forth in any one of SEQ ID NOs: 2-8. For example, the heavy chain variable region may comprise an amino acid sequence set forth in SEQ ID NO: 2, or SEQ ID NO: 3, or SEQ ID NO: 4, or SEQ ID NO: 5, or SEQ ID NO: 6, or SEQ ID NO: 7 or SEQ ID NO: 8. A preferred heavy chain variable region comprises an amino acid sequence set forth in SEQ ID NO: 8, wherein at least one amino acid e.g., 1, 2, 3, 4, 5, 6, 7, 8, 9, 10, 11, 12, 13, 14, 15, 16, 17, 18, 19, 20, 21, 22, 23 or all amino acid, residues designated 'Xaa' is/are different to the corresponding amino acid position set forth in SEQ ID NO: 1. For example, the heavy chain variable region may comprise an amino acid sequence set forth in SEQ ID NO: 8 wherein all of the amino acid residues designated 'Xaa' are different to the corresponding amino acid position set forth in SEQ ID NO: 1. A particularly preferred heavy chain variable region comprises an amino acid sequence set forth SEQ ID NO: 6. Another particularly preferred heavy chain variable region comprises an amino acid sequence set forth SEQ ID NO: 7.

Alternatively or in addition, the antibodies comprise an immunoglobulin light chain comprising a variable region comprising an amino acid sequence having at least 95% identity to a sequence set forth in any one of SEQ ID NOs: 10-17. Preferably, the immunoglobulin light chain comprises a variable region comprising 3 CDRs of murine IP14 set forth in SEQ ID NOs: 21-23. For example, the antibodies comprise an immunoglobulin light chain comprising a variable region comprising an amino acid sequence set forth in any one of SEQ ID NOs: 10-17. For example, the light chain variable region comprises an amino acid sequence set forth SEQ ID NO: 10, or SEQ ID NO: 11, or SEQ ID NO: 12, or SEQ ID NO: 13, or SEQ ID NO: 14, or SEQ ID NO: 15 or SEQ ID NO: 16, or SEQ ID NO: 17. A preferred light chain variable region comprises an amino acid sequence set forth in SEQ ID NO: 12. Another preferred light chain variable region comprises an amino acid sequence set forth SEQ ID NO: 17.

In one example, an antibody of the disclosure is designated IP14-H1L1, which comprises an immunoglobulin heavy chain comprising a variable region comprising an amino acid sequence set forth in SEQ ID NO: 2 and an immunoglobulin light chain comprising a variable region comprising an amino acid sequence set forth in SEQ ID NO: 10.

In one example, an antibody of the disclosure is designated IP14-H1L2, which comprises an immunoglobulin heavy chain comprising a variable region comprising an amino acid sequence set forth in SEQ ID NO: 2 and an immunoglobulin light chain comprising a variable region comprising an amino acid sequence set forth in SEQ ID NO: 11.

In one example, an antibody of the disclosure is designated IP14-H1L3, which comprises an immunoglobulin heavy chain comprising a variable region comprising an amino acid sequence set forth in SEQ ID NO: 2 and an immunoglobulin light chain comprising a variable region comprising an amino acid sequence set forth in SEQ ID NO: 12.

In one example, an antibody of the disclosure is designated IP14-H1L4, which comprises an immunoglobulin heavy chain comprising a variable region comprising an amino acid sequence set forth in SEQ ID NO: 2 and an immunoglobulin light chain comprising a variable region comprising an amino acid sequence set forth in SEQ ID NO: 13.

In one example, an antibody of the disclosure is designated IP14-H1L5, which comprises an immunoglobulin heavy chain comprising a variable region comprising an amino acid sequence set forth in SEQ ID NO: 2 and an immunoglobulin light chain comprising a variable region comprising an amino acid sequence set forth in SEQ ID NO: 14.

In one example, an antibody of the disclosure is designated IP14-H1L6, which comprises an immunoglobulin heavy chain comprising a variable region comprising an amino acid sequence set forth in SEQ ID NO: 2 and an immunoglobulin light chain comprising a variable region comprising an amino acid sequence set forth in SEQ ID NO: 15.

In one example, an antibody of the disclosure is designated IP14-H1L7, which comprises an immunoglobulin heavy chain comprising a variable region comprising an amino acid sequence set forth in SEQ ID NO: 2 and an immunoglobulin light chain comprising a variable region comprising an amino acid sequence set forth in SEQ ID NO: 16.

In one example, an antibody of the disclosure is designated IP14-H1L8, which comprises an immunoglobulin heavy chain comprising a variable region comprising an amino acid sequence set forth in SEQ ID NO: 2 and an immunoglobulin light chain comprising a variable region comprising an amino acid sequence set forth in SEQ ID NO: 17.

In one example, an antibody of the disclosure is designated IP14-H2L1, which comprises an immunoglobulin heavy chain comprising a variable region comprising an amino acid sequence set forth in SEQ ID NO: 3 and an immunoglobulin light chain comprising a variable region comprising an amino acid sequence set forth in SEQ ID NO: 10

In one example, an antibody of the disclosure is designated IP14-H2L2, which comprises an immunoglobulin heavy chain comprising a variable region comprising an amino acid sequence set forth in SEQ ID NO: 3 and an immunoglobulin light chain comprising a variable region comprising an amino acid sequence set forth in SEQ ID NO: 11.

In one example, an antibody of the disclosure is designated IP14-H2L3, which comprises an immunoglobulin heavy chain comprising a variable region comprising an amino acid sequence set forth in SEQ ID NO: 3 and an immunoglobulin light chain comprising a variable region comprising an amino acid sequence set forth in SEQ ID NO: 12.

In one example, an antibody of the disclosure is designated IP14-H2L4, which comprises an immunoglobulin heavy chain comprising a variable region comprising an amino acid sequence set forth in SEQ ID NO: 3 and an immunoglobulin light chain comprising a variable region comprising an amino acid sequence set forth in SEQ ID NO: 13.

In one example, an antibody of the disclosure is designated IP14-H2L5, which comprises an immunoglobulin heavy chain comprising a variable region comprising an amino acid sequence set forth in SEQ ID NO: 3 and an immunoglobulin light chain comprising a variable region comprising an amino acid sequence set forth in SEQ ID NO: 14.

In one example, an antibody of the disclosure is designated IP14-H2L6, which comprises an immunoglobulin heavy chain comprising a variable region comprising an amino acid sequence set forth in SEQ ID NO: 3 and an immunoglobulin light chain comprising a variable region comprising an amino acid sequence set forth in SEQ ID NO: 15.

In one example, an antibody of the disclosure is designated IP14-H2L7, which comprises an immunoglobulin heavy chain comprising a variable region comprising an amino acid sequence set forth in SEQ ID NO: 3 and an immunoglobulin light chain comprising a variable region comprising an amino acid sequence set forth in SEQ ID NO: 16.

In one example, an antibody of the disclosure is designated IP14-H2L8, which comprises an immunoglobulin heavy chain comprising a variable region comprising an amino acid sequence set forth in SEQ ID NO: 3 and an immunoglobulin light chain comprising a variable region comprising an amino acid sequence set forth in SEQ ID NO: 17.

In one example, an antibody of the disclosure is designated IP14-H3L1, which comprises an immunoglobulin heavy chain comprising a variable region comprising an amino acid sequence set forth in SEQ ID NO: 4 and an immunoglobulin light chain comprising a variable region comprising an amino acid sequence set forth in SEQ ID NO: 10

In one example, an antibody of the disclosure is designated IP14-H3L2, which comprises an immunoglobulin heavy chain comprising a variable region comprising an amino acid sequence set forth in SEQ ID NO: 4 and an immunoglobulin light chain comprising a variable region comprising an amino acid sequence set forth in SEQ ID NO: 11.

In one example, an antibody of the disclosure is designated IP14-H3L3, which comprises an immunoglobulin heavy chain comprising a variable region comprising an amino acid sequence set forth in SEQ ID NO: 4 and an immunoglobulin light chain comprising a variable region comprising an amino acid sequence set forth in SEQ ID NO: 12.

In one example, an antibody of the disclosure is designated IP14-H3L4, which comprises an immunoglobulin heavy chain comprising a variable region comprising an amino acid sequence set forth in SEQ ID NO: 4 and an immunoglobulin light chain comprising a variable region comprising an amino acid sequence set forth in SEQ ID NO: 13.

In one example, an antibody of the disclosure is designated IP14-H3L5, which comprises an immunoglobulin heavy chain comprising a variable region comprising an amino acid sequence set forth in SEQ ID NO: 4 and an immunoglobulin light chain comprising a variable region comprising an amino acid sequence set forth in SEQ ID NO: 14.

In one example, an antibody of the disclosure is designated IP14-H3L6, which comprises an immunoglobulin heavy chain comprising a variable region comprising an amino acid sequence set forth in SEQ ID NO: 4 and an immunoglobulin light chain comprising a variable region comprising an amino acid sequence set forth in SEQ ID NO: 15.

In one example, an antibody of the disclosure is designated IP14-H3L7, which comprises an immunoglobulin heavy chain comprising a variable region comprising an amino acid sequence set forth in SEQ ID NO: 4 and an immunoglobulin light chain comprising a variable region comprising an amino acid sequence set forth in SEQ ID NO: 16.

In one example, an antibody of the disclosure is designated IP14-H3L8, which comprises an immunoglobulin heavy chain comprising a variable region comprising an amino acid sequence set forth in SEQ ID NO: 4 and an immunoglobulin light chain comprising a variable region comprising an amino acid sequence set forth in SEQ ID NO: 17.

In one example, an antibody of the disclosure is designated IP14-H4L1, which comprises an immunoglobulin heavy chain comprising a variable region comprising an amino acid sequence set forth in SEQ ID NO: 5 and an immunoglobulin light chain comprising a variable region comprising an amino acid sequence set forth in SEQ ID NO: 10

In one example, an antibody of the disclosure is designated IP14-H4L2, which comprises an immunoglobulin heavy chain comprising a variable region comprising an amino acid sequence set forth in SEQ ID NO: 5 and an immunoglobulin light chain comprising a variable region comprising an amino acid sequence set forth in SEQ ID NO: 11.

In one example, an antibody of the disclosure is designated IP14-H4L3, which comprises an immunoglobulin heavy chain comprising a variable region comprising an amino acid sequence set forth in SEQ ID NO: 5 and an immunoglobulin light chain comprising a variable region comprising an amino acid sequence set forth in SEQ ID NO: 12.

In one example, an antibody of the disclosure is designated IP14-H4L4, which comprises an immunoglobulin heavy chain comprising a variable region comprising an amino acid sequence set forth in SEQ ID NO: 5 and an immunoglobulin light chain comprising a variable region comprising an amino acid sequence set forth in SEQ ID NO: 13.

In one example, an antibody of the disclosure is designated IP14-H4L5, which comprises an immunoglobulin heavy chain comprising a variable region comprising an amino acid sequence set forth in SEQ ID NO: 5 and an immunoglobulin light chain comprising a variable region comprising an amino acid sequence set forth in SEQ ID NO: 14.

In one example, an antibody of the disclosure is designated IP14-H4L6, which comprises an immunoglobulin heavy chain comprising a variable region comprising an amino acid sequence set forth in SEQ ID NO: 5 and an immunoglobulin light chain comprising a variable region comprising an amino acid sequence set forth in SEQ ID NO: 15.

In one example, an antibody of the disclosure is designated IP14-H4L7, which comprises an immunoglobulin heavy chain comprising a variable region comprising an amino acid sequence set forth in SEQ ID NO: 5 and an immunoglobulin light chain comprising a variable region comprising an amino acid sequence set forth in SEQ ID NO: 16.

In one example, an antibody of the disclosure is designated IP14-H4L8, which comprises an immunoglobulin heavy chain comprising a variable region comprising an amino acid sequence set forth in SEQ ID NO: 5 and an immunoglobulin light chain comprising a variable region comprising an amino acid sequence set forth in SEQ ID NO: 17.

In one example, an antibody of the disclosure is designated IP14-H5L1, which comprises an immunoglobulin heavy chain comprising a variable region comprising an amino acid sequence set forth in SEQ ID NO: 6 and an immunoglobulin light chain comprising a variable region comprising an amino acid sequence set forth in SEQ ID NO: 10

In one example, an antibody of the disclosure is designated IP14-H5L2, which comprises an immunoglobulin heavy chain comprising a variable region comprising an amino acid sequence set forth in SEQ ID NO: 6 and an immunoglobulin light chain comprising a variable region comprising an amino acid sequence set forth in SEQ ID NO: 11.

In one example, an antibody of the disclosure is designated IP14-H5L3, which comprises an immunoglobulin heavy chain comprising a variable region comprising an amino acid sequence set forth in SEQ ID NO: 6 and an immunoglobulin light chain comprising a variable region comprising an amino acid sequence set forth in SEQ ID NO: 12.

In one example, an antibody of the disclosure is designated IP14-H5L4, which comprises an immunoglobulin heavy chain comprising a variable region comprising an amino acid sequence set forth in SEQ ID NO: 6 and an immunoglobulin light chain comprising a variable region comprising an amino acid sequence set forth in SEQ ID NO: 13.

In one example, an antibody of the disclosure is designated IP14-H5L5, which comprises an immunoglobulin heavy chain comprising a variable region comprising an amino acid sequence set forth in SEQ ID NO: 6 and an immunoglobulin light chain comprising a variable region comprising an amino acid sequence set forth in SEQ ID NO: 14.

In one example, an antibody of the disclosure is designated IP14-H5L6, which comprises an immunoglobulin heavy chain comprising a variable region comprising an amino acid sequence set forth in SEQ ID NO: 6 and an immunoglobulin light chain comprising a variable region comprising an amino acid sequence set forth in SEQ ID NO: 15.

In one example, an antibody of the disclosure is designated IP14-H5L7, which comprises an immunoglobulin heavy chain comprising a variable region comprising an amino acid sequence set forth in SEQ ID NO: 6 and an immunoglobulin light chain comprising a variable region comprising an amino acid sequence set forth in SEQ ID NO: 16.

In one example, an antibody of the disclosure is designated IP14-H5L8, which comprises an immunoglobulin heavy chain comprising a variable region comprising an amino acid sequence set forth in SEQ ID NO: 6 and an immunoglobulin light chain comprising a variable region comprising an amino acid sequence set forth in SEQ ID NO: 17. It has been shown that the antibody designated IP14-H5L8 is particularly effective at binding human midkine protein. For example, it has been shown that IP14-H5L8 has better binding affinity than the murine IP14 precursor antibody for huMK, and is more effective at inhibiting UMR-106 cell migration in the presence of midkine protein.

In one example, an antibody of the disclosure is designated IP14-H6L1, which comprises an immunoglobulin heavy chain comprising a variable region comprising an amino acid sequence set forth in SEQ ID NO: 7 and an immunoglobulin light chain comprising a variable region comprising an amino acid sequence set forth in SEQ ID NO: 10.

In one example, an antibody of the disclosure is designated IP14-H6L2, which comprises an immunoglobulin heavy chain comprising a variable region comprising an amino acid sequence set forth in SEQ ID NO: 7 and an immunoglobulin light chain comprising a variable region comprising an amino acid sequence set forth in SEQ ID NO: 11.

In one example, an antibody of the disclosure is designated IP14-H6L3, which comprises an immunoglobulin heavy chain comprising a variable region comprising an amino acid sequence set forth in SEQ ID NO: 7 and an immunoglobulin light chain comprising a variable region comprising an amino acid sequence set forth in SEQ ID NO: 12. It has been shown that the antibody designated IP14-H6L83 is particularly effective at binding human midkine protein. For example, it has been shown that IP14-H6L3 has better binding affinity than the murine IP14 precursor antibody for huMK, and is more effective at inhibiting UMR-106 cell migration in the presence of midkine protein.

In one example, an antibody of the disclosure is designated IP14-H6L4, which comprises an immunoglobulin heavy chain comprising a variable region comprising an amino acid sequence set forth in SEQ ID NO: 7 and an immunoglobulin light chain comprising a variable region comprising an amino acid sequence set forth in SEQ ID NO: 13.

In one example, an antibody of the disclosure is designated IP14-H6L5, which comprises an immunoglobulin heavy chain comprising a variable region comprising an amino acid sequence set forth in SEQ ID NO: 7 and an immunoglobulin light chain comprising a variable region comprising an amino acid sequence set forth in SEQ ID NO: 14.

In one example, an antibody of the disclosure is designated IP14-H6L6, which comprises an immunoglobulin heavy chain comprising a variable region comprising an amino acid sequence set forth in SEQ ID NO: 7 and an immunoglobulin light chain comprising a variable region comprising an amino acid sequence set forth in SEQ ID NO: 15.

In one example, an antibody of the disclosure is designated IP14-H6L7, which comprises an immunoglobulin heavy chain comprising a variable region comprising an amino acid sequence set forth in SEQ ID NO: 7 and an immunoglobulin light chain comprising a variable region comprising an amino acid sequence set forth in SEQ ID NO: 16.

In one example, an antibody of the disclosure is designated IP14-H6L8, which comprises an immunoglobulin heavy chain comprising a variable region comprising an amino acid sequence set forth in SEQ ID NO: 7 and an immunoglobulin light chain comprising a variable region comprising an amino acid sequence set forth in SEQ ID NO: 17. It has been shown that the antibody designated IP14-H6L8 is particularly effective at binding human midkine protein. For example, it has been shown that IP14-H6L8 has better binding affinity than the murine IP14 precursor antibody for huMK, and is more effective at inhibiting UMR-106 cell migration in the presence of midkine protein.

The % identity of an immunoglobulin chain of an antibody is determined by GAP (Needleman and Wunsch, 1970) analysis (GCG program) with a gap creation penalty=5, and a gap extension penalty=0.3. The query sequence is at least 50 amino acids in length, and the GAP analysis aligns the two sequences over a region of at least 50 amino acids. Even more preferably, the query sequence is at least 100 amino acids in length and the GAP analysis aligns the two sequences over a region of at least 100 amino acids. Most preferably, the two sequences are aligned over their entire length.

With regard to a defined immunoglobulin chain of an antibody, it will be appreciated that % identity figures higher than those provided above will encompass preferred embodiments. Thus, where applicable, in light of the minimum % identity figures, it is preferred that the immunoglobulin chain comprises an amino acid sequence which is at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In another embodiment, one residue is added to the nominated SEQ ID NO, one residue is deleted from the nominated SEQ ID NO, one residue is added and one residue is deleted compared to the nominated SEQ ID NO, two residues are added to the nominated SEQ ID NO, two residues are deleted from the nominated SEQ ID NO, one residue is changed from the nominated SEQ ID NO, two residues are changed from the nominated SEQ ID NO, one residue is changed and one residue is deleted from the nominated SEQ ID NO, or one residue is changed and one residue is added to the nominated SEQ ID NO, or any combination thereof.

In a preferred embodiment, there are no gaps in the alignment. More specifically, the algorithm does not need to create a gap in a contiguous stretch of amino acids to obtain an optimal (highest % identity) alignment.

Amino acid sequence mutants of the antibody and/or immunoglobulin chain of the present disclosure can be prepared by introducing appropriate nucleotide changes into a nucleic acid of the present disclosure, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (altered) polypeptides can be prepared using any technique known in the art. For example, a polynucleotide of the disclosure can be subjected to in vitro mutagenesis. Such in vitro mutagenesis techniques include sub-cloning the polynucleotide into a suitable vector, transforming the vector into a "mutator" strain such as the E. coli XL-1 red (Stratagene) and propagating the transformed bacteria for a suitable number of generations. Products derived from mutated/altered DNA can readily be screened using techniques described herein to determine if they have receptor-binding and/or -inhibitory activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the antibody and/or immunoglobulin chain molecule removed and a different residue inserted in its place. The sites of greatest interest for substitutional mutagenesis include sites identified as important for antigen binding. These sites, especially those falling within a sequence of at least three other identically conserved sites of human antibodies and/or immunoglobulin chains, are preferably substituted in a relatively conservative manner. Such conservative substitutions are shown in Table 1 under the heading of "exemplary substitutions".

TABLE 1

| Exemplary substitutions | |
| --- | --- |
| Original Residue | Exemplary Substitutions |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

Furthermore, if desired, unnatural amino acids or chemical amino acid analogues can be introduced as a substitution or addition into the antibody and/or immunoglobulin chain of the present disclosure. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

In a preferred embodiment, an immunoglobulin light chain variable region described herein is joined directly to an immunoglobulin light chain constant region described herein. Similarly, in a further preferred embodiment an immunoglobulin heavy chain variable region described herein is joined directly to an immunoglobulin heavy chain constant region described herein.

A skilled person will understand that the variable and constant regions of an immunoglobulin heavy or light chain can be joined as described by using standard recombinant DNA technology to create a polynucleotide (encoding the joined variable and constant domains) that can be expressed in a suitable host (to produce the said immunoglobulin chain(s)) or by using peptide chemistry to synthesise the joined variable and constant domains.

Antibodies of the disclosure retain a significant proportion of the binding properties of the parent or precursor antibody, namely monoclonal antibody designated IP14 herein or CSM-4 as described in WO2008/059616. In particular, antibodies of the disclosure retain the ability to specifically bind midkine protein e.g., human midkine and/or mouse midkine, recognized by the parent or precursor antibody used to produce such antibodies. Preferably the antibody of the disclosure exhibits substantially the same or improved binding affinity and avidity as the parent or precursor antibody. Ideally, the affinity ($K_D$) of the antibody for midkine will be greater than the parent antibody affinity for midkine.

Binding affinity can be determined by association (Ka) and dissociation (Kd) rate. Equilibrium affinity constant, K, is the ratio of Ka/Kd. Association (Ka) and dissociation (Kd) rates can be measured using surface plasmon resonance (SPR) (Rich and Myszka, *Curr. Opin. Biotechnol.* 11:54 (2000); *Englebienne, Analyst.* 123:1599 (1998)). Instrumentation and methods for real time detection and monitoring of binding rates are known and are commercially available (BiaCore 2000, Biacore AB, Upsala, Sweden; and Malmqvist, *Biochem. Soc. Trans.* 27:335 (1999)). Methods for assaying binding affinity are well known in the art and include half-maximal binding assays, competition assays, and Scatchard analysis. Suitable antigen binding assays are described in this application (See, for instance, Example 2).

As the skilled person will appreciate, "avidity" relates to the overall strength of interaction between two molecules, such as an antibody and antigen. Avidity depends on both the affinity and the valency of interactions. Furthermore, "affinity" relates to the strength of the binding between a single binding site of a molecule (e.g., an antibody) and a ligand (e.g., an antigen). The affinity of a molecule X for a ligand Y is represented by the dissociation constant ($K_d$), which is the concentration of Y that is required to occupy the combining sites of half the X molecules present in a solution. A smaller $K_d$ indicates a stronger or higher affinity interaction, and a lower concentration of ligand is needed to occupy the sites.

An antibody of the disclosure may also be a heteroconjugate antibody. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 586505). It is contemplated that the antibodies may be prepared in vitro using known methods in synthetic protein chemistry, including those involving crosslinking agents.

It may be desirable to modify an antibody of the disclosure with respect to effector function, so as to enhance, e.g., the effectiveness of the antibody in treating a disorder described herein such as arthritis. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC) (Caron et al., 1992; Shopes, 1992). Homodimeric antibodies with enhanced activity may also be prepared using heterobifunctional cross-linkers as described in Wolff et al. (1993). Alternatively, an antibody can be engineered that has dual Fc regions and may thereby have enhanced complement lysis and ADCC capabilities (Stevenson et al., 1989).

The antibodies of the disclosure are produced by the intervention of man. Thus, they are not expected to occur in nature. Nonetheless, in a preferred embodiment, an antibody or immunoglobulin chain of the disclosure is "substantially purified" or "purified". By "substantially purified" or "purified" we mean an antibody that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. In another embodiment, "substantially purified" or "purified" means that the molecule that is the predominant species in the composition wherein it is found with respect to the class of molecules to which it belongs (i. e., it makes up at least about 50% of the type of molecule in the composition and typically will make up at least about 70%, at least about 80%, at least about 85%, at least about 90%, at least about 95%, or more of the species of molecule, e. g., peptide, in the composition).

Polynucleotides/Nucleic Acids

The present disclosure also provides isolated and/or recombinant polynucleotides encoding the antibodies s disclosed herein. By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the terms "nucleic acid" and "genetic material". The term "recombinant polynucleotide" refers to a polynucleotide comprising a nucleic acid sequence produced, or which is arrived at, by recombinant means.

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide or protein. An exogenous polynucleotide of the disclosure includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the disclosure operably linked to a promoter suitable of driving transcription of the open reading frame in a cell of interest.

In one example, the present disclosure relates to a polynucleotide encoding a polypeptide having an amino acid sequence set forth in any one of SEQ ID NO:2, SEQ ID NO:3, SEQ ID NO:4, SEQ ID NO:5, SEQ ID NO:6, SEQ ID NO:7, SEQ ID NO:8, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, and/or a polynucleotide which encodes a polypeptide having an amino acid sequence which is at least 95% identical to a sequence set forth in any one of SEQ ID NO:2, SEQ ID NO:3, SEQ ID NO:4, SEQ ID NO:5, SEQ ID NO:6, SEQ ID NO:7, SEQ ID NO:8, SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

The present disclosure also relates to a polynucleotide which hybridizes under stringent conditions to (i) a polynucleotide encoding a polypeptide having an amino acid sequence set forth in any one of SEQ ID NO:2, SEQ ID NO:3, SEQ ID NO:4, SEQ ID NO:5, SEQ ID NO:6, SEQ ID NO:7, SEQ ID NO:8, SEQ ID NO:10, SEQ ID NO:11, SEQ ID NO:12, SEQ ID NO:13, SEQ ID NO:14, SEQ ID NO:15, SEQ ID NO:16, and SEQ ID NO:17, and/or a polynucleotide which encodes a polypeptide having an amino acid sequence which is at least 95% identical to a sequence set forth in any one of SEQ ID NO:2, SEQ ID NO:3, SEQ ID NO:4, SEQ ID NO:5, SEQ ID NO:6, SEQ ID NO:7, SEQ ID NO:8, SEQ ID NO:10, SEQ ID NO:11, SEQ ID NO:12, SEQ ID NO:13, SEQ ID NO:14, SEQ ID NO:15, SEQ ID NO:16, and SEQ ID NO:17. The term "stringent hybridization conditions" or "stringent conditions" and the like as used herein refers to parameters with which the art is familiar, including the variation of the hybridization temperature with length of an polynucleotide or oligonucleotide. Nucleic acid hybridization parameters may be found in references which compile such methods, Sambrook, et al., (supra), and Ausubel, et al., (supra). For example, stringent hybridization conditions, as used herein, can refer to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA) and washing twice in 0.2×SSC, 0.1% SDS at 65° C., with each wash step being about 30 min.

Nucleic acid sequences further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode, modified forms and variants thereof.

The nucleic acids of the disclosure can be of various lengths. Nucleic acid lengths typically range from about 20 nucleotides to 20 Kb, or any numerical value or range within or encompassing such lengths, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length, or any numerical value or range or value within or encompassing such lengths. In particular embodiments, a nucleic acid sequence has a length from about 10-20, 20-30, 30-50, 50-100, 100-150, 150-200, 200-250, 250-300, 300-400, 400-500, 500-1000, 1000-2000, nucleotides, or any numerical value or range within or encompassing such lengths.

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as yeast or bacteria, a eukaryote such as an animal or mammalian cell or in a plant).

Production of antibodies

The antibodies of the present disclosure can be produced in a variety of ways, including production and recovery of recombinant polypeptides, and chemical synthesis of the polypeptides.

Antibodies of the disclosure are typically produced by recombinant expression.

In one example, an antibody of the present disclosure is produced by culturing a cell capable of expressing the antibody under conditions effective to produce the antibody, and recovering the antibody. A preferred cell to culture is a recombinant cell of the present disclosure. Effective culture conditions include, but are not limited to, effective media, bioreactor, temperature, pH and oxygen conditions that permit polypeptide production. An effective medium refers to any medium in which a cell is cultured to produce a polypeptide of the present disclosure. Such medium typically comprises an aqueous medium having assimilable carbon, nitrogen and phosphate sources, and appropriate salts, minerals, metals and other nutrients, such as vitamins. Cells of the present disclosure can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

In one example, the antibodies of the disclosure are produced by recombinant expression. Nucleic acids encoding light and heavy chain variable regions e.g., as described herein, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. As used herein, the term "operably linked to" means positioning a control sequence relative to a nucleic acid encoding the immunoglobulin polypeptide such that expression of the nucleic acid is controlled by the control sequence. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the antibodies and/or immunoglobulin chains.

These expression vectors are typically replicable in the host cells either as episomes or as an integral part of the host chromosomal DNA. Commonly, expression vectors contain selection markers (e.g., ampicillin-resistance, hygromycin-resistance, tetracycline resistance, neomycin resistance, G418-resistance, DHFR (dihydrofolate reductase), ADA (adenosine deaminase), GS (gluatamine synthetase)) to permit detection of those cells transformed with the desired DNA sequences (see, e.g., U.S. Pat. No. 4,704,362).

*E. coli* is one prokaryotic host particularly useful for cloning the polynucleotides (e.g., DNA sequences) of the present disclosure. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, a T7 promoter or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization. Another example of yeast useful for expression is *Pichia pastoris*.

In addition to microorganisms, mammalian tissue cell culture may also be used to express and produce the antibodies and/or immunoglobulin chains of the present disclosure (e.g., polynucleotides encoding immunoglobulins or fragments thereof) (see Winnacker, From Genes to Clones, VCH Publishers, N.Y., N.Y. (1987)). Eukaryotic cells are actually preferred, because a number of suitable host cell lines capable of secreting heterologous proteins (e.g., intact immunoglobulins) have been developed in the art, and include CHO cell lines, various Cos cell lines, NSO cells, HEK293 cells, PerC6 cells, HeLa cells, preferably, myeloma cell lines, or transformed B-cells or hybridomas. Preferably, the cells are nonhuman. Expression vectors for these cells can include expression control sequences, such as an origin of replication, a promoter, and an enhancer (Queen et al., 1986), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like (see Co et al., 1992).

Alternatively, antibody-coding sequences can be incorporated in transgenes for introduction into the genome of a transgenic animal and subsequent expression in the milk of the transgenic animal (see, e.g., U.S. Pat. Nos. 5,741,957, 5,304,489, and 5,849,992). Suitable transgenes include coding sequences for light and/or heavy chains in operable linkage with a promoter and enhancer from a mammary gland specific gene, such as casein or beta lactoglobulin.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts (see generally Sambrook et al., supra). Other methods used to transform mammalian cells include the use of polybrene, protoplast fusion, liposomes, electroporation, and microinjection. For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present disclosure can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)).

Isolation/Purification of antibodies

The antibodies of the disclosure are preferably isolated, and, more preferably, provided in a substantially purified form. Methods for isolating and purifying antibodies and proteins are known in the art and/or described herein.

Where an antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibodies prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbour Laboratory, (1988).

The skilled artisan will also be aware that an antibody of the disclosure can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting antibody is then purified using methods known in the art, such as, affinity purification. For example, an immunoglobulin comprising a hexa-his tag is purified by contacting a sample comprising the immunoglobulin with nickel-nitrilotriacetic acid (Ni-NTA) that specifically binds a hexa-his tag immobilized on a solid or semi-solid support, washing the sample to remove unbound antibodies, and subsequently eluting the bound antibodies. Alternatively, or in addition a ligand or antibody that binds to a tag may be used in an affinity purification method.

Conjugates

The present disclosure also provides conjugates of antibodies or binding fragments thereof as described herein according to any embodiment. For example, the present disclosure provides conjugates (immunoconjugates) comprising an antibody of the disclosure conjugated to a therapeutic or diagnostic agent which is directly or indirectly bound to the antibody. Examples of therapeutic agents include, but are not limited to, a cytotoxin, a radioisotope (e.g., iodine-131, yttrium-90 or indium-111), an immunomodulatory agent, an anti-angiogenic agent, an anti-neovascularization and/or other vascularization agent, a toxin, an anti-proliferative agent, a pro-apoptotic agent, a chemotherapeutic agent and a therapeutic nucleic acid.

A cytotoxin includes any agent that is detrimental to (e.g., kills) cells. For a description of these classes of drugs which are well known in the art, and their mechanisms of action, see Goodman et al., Goodman and Gilman's The Pharmacological Basis of Therapeutics, 8th Ed., Macmillan Publishing Co., 1990. Additional techniques relevant to the preparation of antibody immunotoxins are provided in for instance Vitetta (1993) and U.S. Pat. No. 5,194,594.

Suitable chemotherapeutic agents for forming immunoconjugates of the present disclosure include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, Pseudomonas exotoxin, alorin, saporin, modeccin, gelanin, abrin A chain, modeccin A chain, alpha-sarcin. Aleurites fordii proteins, dianthin proteins, Phytolacca americana proteins (PAPI, PAPII, and PAP-S), momordica charantia inhibitor, curcin, crotin, saponaria officinalis inhibitor, gelonin, mitogellin, restrictocin, phenomycin, and enomycin toxins. Preferably, the therapeutic agent is carboplatin.

Examples of suitable angiogenesis inhibitors (anti-angiogenic agents) include, but are not limited to, urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents. Other examples of inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

A variety of radionuclides are available for the production of radioconjugated proteins. Examples include, but are not limited to, low energy radioactive nuclei (e.g., suitable for diagnostic purposes), such as $^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like. Preferably, the radionuclide is a gamma, photon, or positron-emitting radionuclide with a half-life suitable to permit activity or detection after the elapsed time between administration and localization to the imaging site. The present disclosure also encompasses high energy radioactive nuclei (e.g., for therapeutic purposes), such as $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., 1998).

Conjugates of the antibody or functional binding fragment and therapeutic agent are made using a variety of bifunctional protein-coupling agents such as, but not limited to, 4-(4'acetylphenoxy)butanoic acid (AcBut), 3-acetylphenyl acidic acid (AcPac), 4-mercapto-4-methyl-pentanoic acid (Amide), N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene), and derivatives thereof. For example, a ricin immunotoxin can be prepared as described by Vitetta et al. (1987). Carbon-14-labeled 1-isothiocyanatobenzyl-3-methyldiethylene triaminepentaacetic acid (MX-DTPA) is an exemplary chelating agent for conjugation of radionucleotide to the antibody (WO 94/11026).

In another example, an antibody of the disclosure may be conjugated to a "receptor" (such as streptavidin) for utilization in cell pretargeting wherein the antibody-receptor conjugate is administered to the patient, followed by removal of unbound conjugate from the circulation using a clearing agent and then administration of a "ligand" (e.g., avidin) that is conjugated to a therapeutic agent (e.g., a radionucleotide).

In another example, an antibody of the disclosure can be modified to contain additional nonproteinaceous moieties that are known in the art and readily available. Preferably, the moieties suitable for derivatization of the protein are physiologically acceptable polymer, preferably a water soluble polymer. Such polymers are useful for increasing stability and/or reducing clearance (e.g., by the kidney) and/or for reducing immunogenicity of a protein of the disclosure. Non-limiting examples of water soluble polymers include, but are not limited to, polyethylene glycol (PEG), polyvinyl alcohol (PVA), or propropylene glycol (PPG).

In one example, an antibody as described herein according to any embodiment is conjugated or linked to another protein, including another protein of the disclosure or a protein comprising an antibody variable region, such as an antibody or a protein derived therefrom, e.g., as described herein. Other proteins are not excluded. Additional proteins will be apparent to the skilled artisan and include, for example, an immunomodulator or a half-life extending protein or a peptide or other protein that binds to serum albumin amongst others.

Exemplary serum albumin binding peptides or protein are described in US20060228364 or US20080260757.

In another example, an antibody of the disclosure is used to deliver genetic material. The genetic material can be conjugated to the antibody by any technique known in the art. Examples include, but are not limited to, the use of biotin-avidin interaction, formation of disulfide bridges, amine coupling (see, for example, Hendrickson et al., 1995), thiol coupling (see, for example, Niemeyer et al., 2003), or aldehyde-hydrazine interaction (see, for example, Kozlov et al., 2004). Other coupling agents known to those in the art, include m-maleimidobenzoyl N-hydroxysuccinimide ester or related compounds, carbodiimides, such as, 1-ethyl-3-(3-diethylaminopropyl) carbodiimide (EDC), succinimidyl 4-(N-maleimidomethyl) cyclohexane-1-carboxylate (SMCC), and glutaraldehyde cross-linkers.

In one example, an antibody of the disclosure comprises one or more detectable markers to facilitate detection and/or isolation. For example, the compound comprises a fluorescent label such as, for example, fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, fluorescein (5-carboxyfluorescein-N-hydroxysuccinimide ester), rhodamine (5,6-tetramethyl rhodamine). The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm).

Alternatively, or in addition, the antibody as described herein according to any embodiment is labeled with, for example, a fluorescent semiconductor nanocrystal (as described, for example, in U.S. Pat. No. 6,306,610).

Alternatively, or in addition, the antibody is labeled with, for example, a magnetic or paramagnetic compound, such as, iron, steel, nickel, cobalt, rare earth materials, neodymium-iron-boron, ferrous-chromium-cobalt, nickel-ferrous, cobalt-platinum, or strontium ferrite.

In vitro functional assays

Various in vitro assays are available to assess the ability of a candidate antibody of the disclosure to bind midkine protein and/or inhibit midkine activity and/or treat a midkine-related disease or condition.

For example, binding specificity and affinity of the antibodies to human midkine may be assessed by ELISA e.g., as described in Example 2 herein. In this way, the dissociation constant (Kd) of a candidate antibody may be determined.

In another example, the "Kd" or "Kd value" for antibodies of the disclosure is measured by a radiolabeled midkine binding assay (RIA). This assay equilibrates the test antibody with a minimal concentration of radioactive midkine in the presence of a titration series of unlabelled midkine. Following washing to remove unbound midkine, the amount of radioactivity is determined, which is indicative of the Kd of the test antibody.

According to another example the "Kd" or "Kd value" is measured by using surface plasmon resonance assays, e.g., using BIAcore surface plasmon resonance (BIAcore, Inc., Piscataway, N.J.) with immobilized IL-3Rα.

In some examples, antibodies having a similar Kd or a higher Kd than IP-14 are selected, because they are likely to compete for binding to midkine.

In yet another example, a chemotaxis assay can be used to assess the ability of an antibody of the disclosure to block binding of midkine protein to a receptor thereof and/or inhibit function associated with binding of the midkine to the receptor. These assays are based on the functional migration of cells in vitro or in vivo induced by a compound (chemoattractant). Chemotaxis can be assessed by any suitable means, for example, in an assay utilizing a 96-well chemotaxis plate, or using other art-recognized methods for assessing chemotaxis.

Generally, chemotaxis assays monitor the directional movement or migration of a suitable cell into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen. Such assays provide an in vitro approximation of cell "homing".

For example, one can detect or measure inhibition of the migration of cells in a suitable container (a containing means), from a first chamber into or through a microporous membrane into a second chamber which contains a chemoattractant e.g., midkine protein, and an antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3-8 microns, and preferably about 5-8 microns can be used. Pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy and flow cytometry). In one embodiment, the cells are labeled with a detectable label (e.g., radioisotope, fluorescent label, antigen or epitope label), and migration can be assessed in the presence and absence of a candidate antibody by determining the presence of the label adherent to the membrane and/or present in the second chamber using an appropriate method (e.g., by detecting radioactivity, fluorescence, immunoassay). The extent of migration induced or inhibited can be determined relative to a suitable control (e.g., compared to background migration determined in the absence of the antibody, compared to the extent of migration induced by a second compound (i.e., a standard), compared with migration of untransfected cells induced by the antibody).

In one embodiment, a population of cells to which midkine protein binds or which is capable if migrating to midkine protein e.g., a population of UMR106 cells, is placed in a chamber of a cell culture device that is in liquid communication with another chamber comprising midkine protein (chemoattractant). The two chambers are separated by a suitable membrane, e.g., a membrane that mimics the extracellular matrix found in a subject. The amount of cell migration from one chamber to the other through the membrane is assessed in the presence or absence of candidate antibodies. An antibody that prevents or reduces the amount of midkine-mediated cell migration compared to a control sample (containing no antibody) is considered to have midkine inhibitory activity.

An exemplary chemotaxis assay for assessing the ability of a candidate antibody described herein to bind midkine protein is a cell migration assay e.g., as described Example 3 herein, Matsui et al., (2010) *International Archives of Medicine*, 3:12 and US2014/0170144.

As will be apparent to the skilled artisan, methods of screening may involve detecting levels of cell death, cell proliferation and/or cell survival. Such methods are known in the art.

In Vivo functional assays

In another example, the efficacy of an antibody of the disclosure to bind midkine protein and/or to treat a disease or condition is assessed using an in vivo assay.

For example, a candidate antibody of the disclosure may be administered to a non-human mammal (e.g., murine) model of cancer e.g., such as a NCI-H460 xenograft mouse model. A candidate antibody that reduces or alleviates at least one symptom associated with the cancer e.g., tumor size or volume, in the mammalian subject relative to the cancer or symptom thereof in the subject prior to administration and/or in a control mammal to which the candidate antibody has not been administered, is considered suitable for treating the disease or condition.

Midkine-related disorders

The antibodies of the present disclosure inhibit midkine functions and can therefore be used as therapeutic and preventative drugs for midkine-related disease. The term "midkine-related disease" refers to a disease involving midkine functions. Examples of such diseases include: diseases attributed to cell growth or angiogenesis, such as cancers (esophageal cancer, thyroid cancer, urinary bladder cancer, colon cancer, stomach cancer, pancreatic cancer, thoracic cancer, liver cancer, lung cancer, breast cancer, neuroblastoma, glioblastoma, uterine cancer, ovarian cancer, prostatic cancer, and Wilms tumor) and endometriosis; inflammatory diseases or diseases attributed to cell migration or suppression of regulatory T cell function, such as inflammatory diseases of the kidney, acute renal failure, chronic kidney diseases arthritis, autoimmune disease (organ-specific autoimmune disease, etc.), rheumatic arthritis (rheumatoid arthritis (RA) or osteoarthritis (OA)), multiple sclerosis (relapsing-remitting multiple sclerosis, etc.), inflammatory bowel disease (Crohn disease, etc.), systemic lupus erythematosus (SLE), progressive systematic sclerosis (PSS), Sjogren's syndrome, polymyositis (PM), dermatomyositis (DM), polyarteritis nodosa (PN), thyroid disease (Graves disease, etc.), Guillain-Barre syndrome, primary biliary cirrhosis (PBC), idiopathic thrombocytopenic purpura, autoimmune hemolytic anemia, experimental autoimmune myasthenia gravis (EAMG), amyotrophic lateral sclerosis (ALS), type I diabetes mellitus, transplant rejection, postoperative adhesion, endometriosis, psoriasis, lupus, allergy, asthma, and neutrophil dysfunction; and occlusive vascular diseases or diseases attributed to vascular intimal thickening, such as post-revascularization restenosis, coronary occlusive disease, cerebrovascular occlusive disease, renovascular occlusive disease, peripheral occlusive disease, arteriosclerosis, and cerebral infarction. The MK-related disease is preferably cancer, arteriosclerosis, angiogenesis-related disease, angina pectoris, myocardial infarction, cerebral infarction, cerebral hemorrhage, hypertension, nephritis, chronic obstructive pulmonary disease (COPD) or multiple sclerosis.

In one preferred example, the antibodies of the present disclosure inhibit midkine functions and can therefore be used as therapeutic agents in the treatment of cancer e.g., such as those described herein.

In another preferred example, the antibodies of the present disclosure are capable of binding midkine protein and can therefore be used as diagnostic agents to be used in diagnosis or prognosis of cancer e.g., such as those described herein.

Compositions

Suitably, in compositions or methods for administration of the antibodies or conjugates of the disclosure to a mammal, the antibody or conjugate is combined with a pharmaceutically acceptable carrier, diluent and/or excipient, as is understood in the art. Accordingly, one example of the present disclosure provides a pharmaceutical composition comprising the antibody or conjugate thereof combined with a pharmaceutically acceptable carrier, diluent and/or excipient. Alternatively, the antibodies or conjugates of this disclosure can be lyophilized for storage and reconstituted in a suitable carrier prior to use according to art-known lyophilization and reconstitution techniques.

In another example, the disclosure provides a kit comprising a pharmaceutically acceptable carrier, diluent and/or excipient suitable for combining or mixing with the antibody or conjugate prior to administration to the mammal. For example, the antibodies or conjugates of this disclosure can be provided in a lyophilized form for combining or mixing with a pharmaceutically acceptable carrier, diluent and/or excipient prior to administration to the mammal. In this example, the kit may further comprise instructions for use.

In general terms, by "carrier, diluent or excipient" is meant a solid or liquid filler, binder, diluent, encapsulating substance, emulsifier, wetting agent, solvent, suspending agent, coating or lubricant that may be safely administered to any mammal, e.g., a human. Depending upon the particular route of administration, a variety of acceptable carriers, diluents or excipients, known in the art may be used, as for example described in Remington's Pharmaceutical Sciences (Mack Publishing Co. N.J. USA, 1991).

By way of example only, the carriers, diluents or excipients may be selected from a group including sugars (e.g.

sucrose, maltose, trehalose, glucose), starches, cellulose and its derivatives, malt, gelatine, talc, calcium sulphate, oils inclusive of vegetable oils, synthetic oils and synthetic mono- or di-glycerides, lower alcohols, polyols, alginic acid, phosphate buffered solutions, lubricants such as sodium or magnesium stearate, isotonic saline and pyrogen-free water. For example, the carrier, diluent or excipient is compatible with, or suitable for, parenteral administration. Parenteral administration includes any route of administration that is not through the alimentary canal. Non-limiting examples of parenteral administration include injection, infusion and the like. By way of example, administration by injection includes intravenous, intra-arterial, intramuscular and subcutaneous injection. Also contemplated is delivery by a depot or slow-release formulation which may be delivered intradermally, intramuscularly and subcutaneously, for example.

Combination Therapies

The antibodies, conjugates and compositions of the present disclosure can also be administered as part of a combinatorial therapy with other agents useful for treating a disease or condition, e.g., cancer, either as combined or additional treatment steps or as additional components of a therapeutic formulation. Such other therapies/agents will be well-known to those skilled in the art.

For example, the other compound is an anti-inflammatory compound. Alternatively, or additionally, the other compound is an immunosuppressant. Alternatively, or additionally, the other compound is a chemotherapeutic agent, such as carboplatin.

Dosages and Regimens

For the prevention or treatment of a disease or condition or relapse thereof, the appropriate dosage of an active agent (e.g., an antibody or conjugate of the disclosure), will depend on the type of disease to be treated, the severity and course of the disease, whether the active agent is administered for preventive or therapeutic purposes, previous therapy, the patient's clinical history and response to the active agent, and the discretion of the attending physician. Typically, a therapeutically effective amount of the antibody or conjugate will be administered. The phrase "a therapeutically effective amount" refers to an amount sufficient to promote, induce, and/or enhance treatment or other therapeutic effect in the subject being treated. The therapeutically effective amount should be large enough to produce the desired effect but should not be so large as to cause adverse side effects. The particular dosage regimen, i.e., dose, timing, and repetition, will depend on the particular individual and that individual's medical history as assessed by a physician. Typically, a clinician will administer an active agent (e.g., antibody or conjugate comprising same) until a dosage is reached that achieves the desired result.

Generally, the dosage will vary with the age, condition, sex and extent of the disease in the patient and can be determined by one of skill in the art. The dosage can be adjusted by the individual physician in the event of any complication. For in vivo administration of the antibodies or conjugates described herein, normal dosage amounts may vary from about 10 ng/kg up to about 100 mg/kg of an individual's body weight or more per day. Exemplary dosages and ranges thereof are described herein. For repeated administrations over several days or longer, depending on the severity of the disease or disorder to be treated, the treatment can be sustained until a desired suppression of symptoms is achieved.

In some examples, an antibody or conjugate as described herein is administered at an initial (or loading) dose of between about 1 mg/kg to about 30 mg/kg, such as from about 1 mg/kg to about 10 mg/kg, or about 2 mg/kg or about 3 mg/kg or 4 mg/kg or 5 mg/kg. The antibody or conjugate can then be administered at a maintenance dose of between about 0.0001 mg/kg to about 1 mg/kg, such as from about 0.0005 mg/kg to about 1 mg/kg, for example, from about 0.001 mg/kg to about 1 mg/kg, such as about 0.005 mg/kg to about 1 mg/kg, for example from about 0.1 mg/kg to about 1 mg/kg, such as about 0.2 mg/kg or 0.3 mg/kg or 0.4 mg/kg or 0.5 mg/kg. The maintenance doses may be administered every 7-30 days, such as, every 10-15 days, for example, every 10 or 11 or 12 or 13 or 14 or 15 days.

Dosages for a particular antibody or conjugate may be determined empirically in mammals who have been given one or more administrations of the respective antibody or conjugate. To assess efficacy of an antibody or conjugate of the disclosure, a clinical symptom of a disease or condition being treated e.g., cancer, can be monitored. For example, efficacy of an antibody or conjugate of the disclosure in treatment of cancer may be assessed based on tumor size and/or using diagnostic or prognostic biomarkers of cancer.

Administration of an antibody or conjugate according to the methods of the present disclosure can be continuous or intermittent, depending, for example, on the recipient's physiological condition, whether the purpose of the administration is therapeutic or prophylactic, and other factors known to skilled practitioners. The administration of an antibody or conjugate may be essentially continuous over a preselected period of time or may be in a series of spaced doses.

A variety of routes of administration are possible including, but not necessarily limited to, oral, dietary, topical, parenteral (e.g., intravenous, intraarterial, intramuscular, subcutaneous injection), inhalation (e.g., intrabronchial, intraocular, intranasal or oral inhalation, intranasal drops), depending on the disease or condition to be treated. Other suitable methods of administration can also include rechargeable or biodegradable devices and slow release polymeric devices.

Diagnostic tests

It will be appreciated that the antibodies and conjugates described herein have value in detecting the presence or absence of midkine, particularly for diagnostic applications. Typically, diagnostic assays entail detecting the formation of a complex resulting from the binding of an antibody or fragment thereof to midkine. For diagnostic purposes, the antibodies or conjugates can be labelled or unlabelled.

The antibodies or conjugates can be directly labelled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654 and 4,098,876). For example, the antibodies may be used in diagnostic assays such as ELISAs, radioimmunoassays, immunohistological methods, and western blotting. Immunohistochemistry of tissue samples may also be used in the diagnostic methods of the present disclosure. When unlabelled, the antibodies or conjugates can be detected using suitable means, as in agglutination assays, for example. Unlabelled antibodies or conjugates of the disclosure can also be used in combination with another (i.e., one or more) suitable reagent which can be used to detect the antibody or conjugate, such as a labelled antibody (e.g., a secondary antibody) reactive with the first antibody (e.g., anti-idiotype antibodies or other antibodies that are specific for the unlabelled immunoglobulin) or other suitable reagent (e.g., labelled protein A).

With regard to imaging agents, any suitable agents which can be used include, but are not limited to, an MRI agent, a CT imaging agent, an optical imaging agent, an ultrasound imaging agent, a paraCEST imaging agent, and a combination thereof. In an embodiment, the agent is a proton based MRI or paraCEST agent comprising a chelate of a paramagnetic metal selected from the group consisting of scandium, titanium, vanadium, chromium, manganese, iron, cobalt, nickel, copper, molybdenum, ruthenium, cerium, indium, praseodymium, neodymium, promethium, samarium, europium, gadolinium, terbium, dysprosium, holmium, erbium, thulium, and ytterbium. In a further embodiment, the agent can be CT imaging agent comprising an iodinated oil nanoparticles or an entrapped solid metal particle. A further example of imaging agents useful for the present disclosure is halocarbon-based nanoparticle such as PFOB or other fluorine-based MRI agents.

It will be appreciated that a variety of tissue samples or liquids collected as biopsies from test subjects can be used as specimens for the diagnostic agent of the present disclosure. The biopsies used are not particularly limited as long as they are targeted by the immunological measurement of midkine. Examples thereof can include tissues, blood, urine, serous fluids, spinal fluids, synovial fluids, aqueous humor, lacrimal fluids, saliva or fractionated or processed products thereof. Analysis using the diagnostic agent can be conducted qualitatively, quantitatively, or semi-quantitatively.

Kits for use in detecting the presence of a midkine protein in a biological sample can also be prepared. Such kits may include an antibody or conjugate of the disclosure which binds to human midkine, as well as one or more ancillary reagents suitable for detecting the presence of a complex between the antibody, fragment or conjugate and midkine. The antibodies and/or conjugates of the present disclosure can be provided in lyophilized form, either alone or in combination with additional antibodies specific for other epitopes. The antibodies and/or conjugates, which can be labelled or unlabelled, can be included in the kits with adjunct ingredients (e.g., buffers, such as Tris, phosphate and carbonate, stabilizers, excipients, biocides and/or inert proteins, e.g., bovine serum albumin). For example, the antibodies and/or conjugates can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the antibody or conjugate is employed, such an antibody can be provided in the kit, for instance in a separate vial or container. The second antibody, if present, is typically labelled, and can be formulated in an analogous manner with the antibody formulations described herein.

The present invention will now be described more specifically with reference to the following non-limiting Examples.

EXAMPLES

Example 1. Production of Humanised IP14 Antibodies

Design of humanized variants

A number of humanized variants of the light (L) and heavy (H) variable (v) domains of murine IP14 (mIP14) antibody were designed in silico. mIP14 is the same as antibody designated CSM-4 in WO2008/059616. The humanised VH and VL sequences were determined by:
(i) identifying the CDR sequences, vernier zone (VZ) and unusual sequences (US) in the murine antibody mIP14;
(ii) identifying suitable human acceptor sequences; and
(iii) grafting one or more of the murine CDR sequences, and optionally the VZ and/or US sequence(s), from mIP14 onto the human acceptor sequences, where appropriate.

Z-scores were then derived for each of the humanised VH and VL domains to indicate the degree of "humanness" of a sequence: a Z-score of 0 corresponds to a sequence that is on average similar to the repertoire of human sequences, a positive Z-score corresponds to sequences that are on average highly identical to human sequences, and a negative Z-score corresponds to sequences that are on average less typical of human sequences (Abhinandan et al., (2007) *J. Mol. Biol.*, 369:852-862).

The humanised variants of the VH and VL domains are presented in Tables 2 and 3 respectively. Z-scores for each of the humanised VH and VL variants are also presented in FIG. 1.

TABLE 2

Humanised mIP14 VH sequences evaluated

| Variant name | SEQ ID NO: | Acceptor | CDR | VZ | US | Z-score |
|---|---|---|---|---|---|---|
| IP14 VHhuV1 | SEQ ID NO: 2 | IMGT-IGHV1-46 | X | X | X | −1.2 |
| IP14 VHhuV2 | SEQ ID NO: 3 | IMGT-IGHV1-46 | X | X |  | −1.0 |
| IP14 VHhuV3 | SEQ ID NO: 4 | IMGT-IGHV1-46 | X |  |  | −0.6 |
| IP14 VHhuV4 | SEQ ID NO: 5 | IMGT-IGHV1-46 | CDR3 only |  |  | 0.0 |
| IP14 VHhuV5 | SEQ ID NO: 6 | FW1.4 | X | X | X | −0.1 |
| IP14 VHhuV6 | SEQ ID NO: 7 | IMGT-IGHV3-11 | X | X | X | 0.0 |

TABLE 3

Humanised mIP14 VL sequences evaluated

| Variant name | SEQ ID NO: | Acceptor | CDR | VZ | US | Z-score |
|---|---|---|---|---|---|---|
| IP14 VLhuV1 | SEQ ID NO: 9 | IMGT-IGKV1-NL4 | X | X | X | −0.6 |
| IP14 VLhuV2 | SEQ ID NO: 10 | IMGT-IGKV1-NL4 | X | X |  | 0.0 |
| IP14 VLhuV3 | SEQ ID NO: 11 | IMGT-IGKV1-NL4 | X |  |  | 0.4 |

TABLE 3-continued

Humanised mIP14 VL sequences evaluated

| Variant name | SEQ ID NO: | Acceptor | CDR | VZ | US | Z-score |
|---|---|---|---|---|---|---|
| IP14 VLhuV4 | SEQ ID NO: 12 | VBASE-DPK26 | X | X | X | −1.3 |
| IP14 VLhuV5 | SEQ ID NO: 13 | IMGT-IGKV1-NL4 | CDR3 only | | | 1.0 |
| IP14 VLhuV6 | SEQ ID NO: 14 | FW1.4 | X | X | X | −0.1 |
| IP14 VLhuV7 | SEQ ID NO: 15 | HuCal Vk3 | X | X | X | 0.1 |
| IP14 VLhuV8 | SEQ ID NO: 16 | HuCal Vk3 | X | X | | 0.5 |

Gene synthesis

Each variable domain described in Table 2 and Table 3 was sequence optimised for expression in mammalian cells and a DNA sequence encoding each variable domain was synthesized and provided in a suitable cloning vector along with sequencing data. Upon receipt, cloning vectors were verified by restriction analysis and propagated in DH5a competent E. coli cells.

Construction of Expression Vectors

Humanised VH and VL domain DNA fragments for subcloning were obtained from the cloning vector by digestion with SacI and PstI, followed by treatment with T4 polymerase for blunting the 5' end of each fragment. The blunted humanised VH domain fragments were then subjected to a second digest with NheI, and the blunted humanised VL domain fragments were subjected to a second digest with BsiWI. The digests were separated by gel electrophoresis, and the relevant fragments were excised and purified.

To construct the IgG expression vectors, the purified DNA fragments encoding the humanised VH domains were subcloned with the human IgG heavy constant domain, and the purified DNA fragments encoding the humanised VL domains were subcloned with the human kappa light constant domain. The expression vector used was proprietary to Biotecnol SA. Ligations of the respective fragments were performed and the resulting ligation was introduced into DH5a chemically competent E. coli cells by heat shock at 42° C., which were subsequently plated and incubated overnight at 37° C. Resulting colonies were screened by PCR using appropriate primers to identify those colonies positive for the insert. The colonies determined to be positive for the insert were grown in small volume culture, after which plasmid DNA extracted, purified and analysed by restriction digest to confirm the presence of the insert. A number of colonies identified as being positive for the insert by restriction analysis were also sequenced to identify and confirm the presence of the correct sequence. A plasmid bank for each of the humanised VH and VL chain IgG vectors was generated, from which required amounts of plasmid DNA for production of the IgGs by transient culture was cultured and purified.

Vectors were successfully constructed for 49 IgG variants, consisting of 1 mouse-human chimeric mAb and 48 humanised mIP14 antibodies. The 48 humanised mIP14 antibodies are presented in Table 4.

TABLE 4

Humanised mIP14 antibodies

| Humanised mIP14 Ab | VH variant | VL variant |
|---|---|---|
| IP14-H1L1 | IP14 VHhuV1 | IP14 VLhuV1 |
| IP14-H1L2 | IP14 VHhuV1 | IP14 VLhuV2 |
| IP14-H1L3 | IP14 VHhuV1 | IP14 VLhuV3 |
| IP14-H1L4 | IP14 VHhuV1 | IP14 VLhuV4 |
| IP14-H1L5 | IP14 VHhuV1 | IP14 VLhuV5 |
| IP14-H1L6 | IP14 VHhuV1 | IP14 VLhuV6 |
| IP14-H1L7 | IP14 VHhuV1 | IP14 VLhuV7 |
| IP14-H1L8 | IP14 VHhuV1 | IP14 VLhuV8 |
| IP14-H2L1 | IP14 VHhuV2 | IP14 VLhuV1 |
| IP14-H2L2 | IP14 VHhuV2 | IP14 VLhuV2 |
| IP14-H2L3 | IP14 VHhuV2 | IP14 VLhuV3 |
| IP14-H2L4 | IP14 VHhuV2 | IP14 VLhuV4 |
| IP14-H2L5 | IP14 VHhuV2 | IP14 VLhuV5 |
| IP14-H2L6 | IP14 VHhuV2 | IP14 VLhuV6 |
| IP14-H2L7 | IP14 VHhuV2 | IP14 VLhuV7 |
| IP14-H2L8 | IP14 VHhuV2 | IP14 VLhuV8 |
| IP14-H3L1 | IP14 VHhuV3 | IP14 VLhuV1 |
| IP14-H3L2 | IP14 VHhuV3 | IP14 VLhuV2 |
| IP14-H3L3 | IP14 VHhuV3 | IP14 VLhuV3 |
| IP14-H3L4 | IP14 VHhuV3 | IP14 VLhuV4 |
| IP14-H3L5 | IP14 VHhuV3 | IP14 VLhuV5 |
| IP14-H3L6 | IP14 VHhuV3 | IP14 VLhuV6 |
| IP14-H3L7 | IP14 VHhuV3 | IP14 VLhuV7 |
| IP14-H3L8 | IP14 VHhuV3 | IP14 VLhuV8 |
| IP14-H4L1 | IP14 VHhuV4 | IP14 VLhuV1 |
| IP14-H4L2 | IP14 VHhuV4 | IP14 VLhuV2 |
| IP14-H4L3 | IP14 VHhuV4 | IP14 VLhuV3 |
| IP14-H4L4 | IP14 VHhuV4 | IP14 VLhuV4 |
| IP14-H4L5 | IP14 VHhuV4 | IP14 VLhuV5 |
| IP14-H4L6 | IP14 VHhuV4 | IP14 VLhuV6 |
| IP14-H4L7 | IP14 VHhuV4 | IP14 VLhuV7 |
| IP14-H4L8 | IP14 VHhuV4 | IP14 VLhuV8 |
| IP14-H5L1 | IP14 VHhuV5 | IP14 VLhuV1 |
| IP14-H5L2 | IP14 VHhuV5 | IP14 VLhuV2 |
| IP14-H5L3 | IP14 VHhuV5 | IP14 VLhuV3 |
| IP14-H5L4 | IP14 VHhuV5 | IP14 VLhuV4 |
| IP14-H5L5 | IP14 VHhuV5 | IP14 VLhuV5 |
| IP14-H5L6 | IP14 VHhuV5 | IP14 VLhuV6 |
| IP14-H5L7 | IP14 VHhuV5 | IP14 VLhuV7 |
| IP14-H5L8 | IP14 VHhuV5 | IP14 VLhuV8 |
| IP14-H6L1 | IP14 VHhuV6 | IP14 VLhuV1 |
| IP14-H6L2 | IP14 VHhuV6 | IP14 VLhuV2 |
| IP14-H6L3 | IP14 VHhuV6 | IP14 VLhuV3 |
| IP14-H6L4 | IP14 VHhuV6 | IP14 VLhuV4 |
| IP14-H6L5 | IP14 VHhuV6 | IP14 VLhuV5 |
| IP14-H6L6 | IP14 VHhuV6 | IP14 VLhuV6 |
| IP14-H6L7 | IP14 VHhuV6 | IP14 VLhuV7 |
| IP14-H6L8 | IP14 VHhuV6 | IP14 VLhuV8 |

Production of humanised anti-MK antibodies 50 ml mammalian cell cultures were transfected with equal amounts of the purified respective light and heavy chain plasmids and incubated at 37° C., 10% $CO_2$. After 7 days, cultures were harvest by centrifugation. For each culture the clarified liquid phase, approximately 30-45 ml, was purified by Protein A affinity chromatography using 1 ml columns. Following appropriate equilibration, loading and washing, elution of the captured IgG from the column was achieved with low pH followed by immediate neutralisation of the eluate. The final elution volume for each structure was 5.5 ml.

Analysis of IgG products

The protein A purified eluates, IgG product, were analysed for each antibody by analytical size exclusion (anSEC) and SDS-PAGE. The anSEC was performed on an HPLC system by injection of 100 µl of the eluate on a 25 cm analytical size exclusion column. The retention time of the peaks separated and detected at 280 nm was compared with an IgG standard. The AUC of the peak/s was converted to estimate the concentration of IgG in the protein A eluate using the theoretical extinction coefficient. The concentration of IgG in protein A eluate for each of the humanised mIP14 antibodies is presented in Table 5.

TABLE 5

Expression yields for humanised mIP14 antibodies

| IP14 | Lv0 | Lv1 | Lv2 | Lv3 | Lv4 | Lv5 | Lv6 | Lv7 | Lv8 |
|---|---|---|---|---|---|---|---|---|---|
| Hv0 | 26 mg/L | 18 mg/L | 23 mg/L | 15 mg/L | 33 mg/L |  | 49 mg/L | 29 mg/L | 28 mg/L |
| Hv1 |  | 18 mg/L | 9 mg/L | 12 mg/L | 25 mg/L | 31 mg/L | 35 mg/L | 39 mg/L | 40 mg/L |
| Hv2 |  | 42 mg/L | 37 mg/L | 28 mg/L | 46 mg/L | 49 mg/L | 40 mg/L | 46 mg/L | 42 mg/L |
| Hv3 |  | 5 mg/L | 12 mg/L | 7 mg/L | 35 mg/L | 36 mg/L | 44 mg/L | 42 mg/L | 34 mg/L |
| Hv4 |  | 2 mg/L | 6 mg/L | 4 mg/L | 23 mg/L | 33 mg/L | 25 mg/L | 39 mg/L | 28 mg/L |
| Hv5 |  | 29 mg/L | 20 mg/L | 23 mg/L | 39 mg/L | 35 mg/L | 45 mg/L | 41 mg/L | 41 mg/L |
| Hv6 |  | 32 mg/L | 34 mg/L | 22 mg/L | 31 mg/L | 39 mg/L | 34 mg/L | 42 mg/L | 37 mg/L |

The relative level of monomer was also determined for humanised mIP14 antibodies comprising Hv5 and Hv6 heavy chain variants by comparing the area of the main, monomer peak, relative to the total area for all peaks. SDS-PAGE of the protein A eluates was performed in reducing and non-reducing conditions, loading up to 3.5 µg of each purified structure based on concentrations determined by anSEC previously. The Molecular Weight Marker (MWM) SeeBlue® Plus2 (Invitrogen) was used to show the molecular weight and an IgG standard was used as a control.

The SDS-PAGE analysis revealed that humanised light chain variants Lv1, Lv4, Lv6 and Lv7 had N-glycolsylation (FIG. 2).

Western-Blot for the promising candidates was performed in non-reducing conditions and incubated with anti-Fc-HRP conjugated antibody.

Example 2. Binding of Humanised Anti-MK Antibodies to Human and Murine MK

The binding specificity and affinity of the humanised anti-MK antibodies to recombinant human MK (huMK) and murine MK (muMK) was assessed by ELISA. ELISA plates (Nunc Immuno MaxiSorp 96 well flat-bottom were coated with 100 uL of 2 ug/mL of either huMK or muMK in 2% BSA/PBS (overnight at room temperature). After washing, blocking (1 h at 37° C.), and washing again, the humanised anti-MK and chimeric antibodies described in Example 1 were analysed for binding to huMK or muMK at concentrations ranging between 3 µg/ml and 0.00004 µg/ml in 2% BSA/PBS (1 h at 37° C.). After washing, the binding of antibody was detected with goat anti-mouse IgG (Fab specific)-HRP conjugate (Sigma, Cat. No. A9917) and Sigma-Fast OPD substrate (Sigma, Cat. No. P9187). The reaction was stopped with 3 M HCl, absorbance read at 490 nm on a Dynex Technologies MRX TC II plate reader and the binding curves plotted. Binding affinity data for the humanised anti-MK antibodies to huMK and muMK are presented in Table 6 and Table 7 respectively, and in FIG. 3.

TABLE 6

Binding affinity of humanised mIP14 antibodies for huMK

| IP14 | Lv0 | Lv1 | Lv2 | Lv3 | Lv4 | Lv5 | Lv6 | Lv7 | Lv8 |
|---|---|---|---|---|---|---|---|---|---|
| Hv0 | 104 | 93 | 95 | 90 | 108 |  | 132 | 92 | 80 |
| Hv1 |  | 56 | 65 | 63 | 50 | >10000 | 53 | 43 | 50 |
| Hv2 |  | 93 | 100 | 68 | 53 | >10000 | 54 | 58 | 56 |
| Hv3 |  | 91 | 82 | 5790 | >10000 | >10000 | 5700 | >10000 | >10000 |
| Hv4 |  | >10000 | >10000 | >10000 | >10000 | >10000 | >10000 | >10000 | >10000 |
| Hv5 |  | 62 | 69 | 68 | 69 | >10000 | 73 | 67 | 60 |
| Hv6 |  | 97 | 41 | 70 | 73 | >10000 | 88 | 68 | 42 |

*ELISA EC50 concentrations for each antibody is provided as (pM)

TABLE 7

Binding affinity of humanised mIP14 antibodies for muMK

| IP14 | Lv0 | Lv1 | Lv2 | Lv3 | Lv4 | Lv5 | Lv6 | Lv7 | Lv8 |
|---|---|---|---|---|---|---|---|---|---|
| Hv0 | 130 | | | | | | | | |
| Hv1 | | 44 | 51 | 89 | 81 | >10000 | 87 | 81 | 89 |
| Hv2 | | 90 | 87 | 81 | 78 | >10000 | 73 | 71 | 69 |
| Hv3 | | 120 | 100 | | | | | | |
| Hv4 | | >10000 | >10000 | >10000 | >10000 | >10000 | >10000 | >10000 | >10000 |
| Hv5 | | 52 | 54 | 50 | 51 | >10000 | 44 | 59 | 50 |
| Hv6 | | 32 | 72 | 48 | 51 | >10000 | 48 | 51 | 91 |

*ELISA EC50 concentrations for each antibody is provided as (pM)

Based on production yields, N-glycosylation profiles, binding affinity and Z-scores, the humanised mIP14 antibodies designated hIP14-H1L3, hIP14-H1L8, hIP14-H2L3, hIP14-H2L8, hIP14-H5L3, hIP14-H5L8, hIP14-H6L2, hIP14-H6L3, and hIP14-H6L8 were identified as being preferred candidates. Furthermore, humanised mIP14 antibodies designated hIP14-H5L8, hIP14-H6L3 and hIP14-H6L8 were identified as being particularly preferred candidates.

$K_D$ values for hIP14-H5L8, hIP14-H6L3 and hIP14-H6L8 was then compared with the $K_D$ values obtained for the corresponding murine IP14 precursor antibody and the chimeric antibody using the methods described in Example 2. The binding affinity data is presented in Table 8. As is apparent from Table 7, the humanised mIP14 antibodies designated hIP14-H5L8, hIP14-H6L3, and hIP14-H6L8 were each shown to have better binding affinity than the murine IP14 precursor antibody and the chimeric antibody for huMK and muMK. Based on this finding, these candidate antibodies were produced to 100 mg scale to enable further testing in functional assays to determine biological function.

TABLE 8

Binding affinity of preferred humanised mIP14 antibodies

| $K_D$ (pM) | Human MK | Murine MK |
|---|---|---|
| mIP14 | 144 | 166 |
| cIP14 | 104 | 130 |
| hIP14-H5L8 | 60 | 50 |
| hIP14-H6L3 | 70 | 48 |
| hIP14-H6L8 | 42 | 91 |

Example 3. Inhibition of MK-mediated Migration of UMR106 Cells by Humanised Anti-midkine Antibodies Cell migration assays were performed for each of the preferred candidate humanised IP14 antibodies and the murine IP14 parent antibody to determine the ability of these antibodies to inhibit migration of UMR106 cells to midkine.

Preparation of MK antigens

Human MK mRNAs were prepared from a cultured cell line G-401 derived from Wilms tumor (Tsutsui et al., (1991) Biochem. Biophys. Res. Commun. 176:792-797, 1991). Primers were designed such that they contained a sequence recognized by a restriction enzyme EcoRI (5'-GAATTC-3'). PCR (polymerase chain reaction) of 30 cycles each involving temperature change of 93° C.->37° C.->72° C. was performed using sense PCR primer: 5'-GCGGAATTCAT-GCAGCACCGAGGCTTCCTC-3' (SEQ ID NO: 24), and anti-sense PCR primer: 5'-GCGGAATTCCTAGTCCTTTC-CCTTCCCTTT-3' (SEQ ID NO: 25) and the human MK mRNAs as templates to prepare human MK cDNAs comprising the MK coding region flanked by EcoRI restriction sites.

The MK cDNAs and expression vectors pHIL301 (containing histidine and a neomycin resistance gene; see Japanese Patent Laid-Open No. 2-104292 and EP Patent No. 0339568) for yeast Pichia pastoris GS115 (hereinafter, referred to as "Pichia yeast GS115") were digested with a restriction enzyme EcoRI and then ligated using a ligation kit (manufactured by TAKARABIO INC.) to prepare recombinant expression vectors.

The recombinant expression vectors thus prepared were introduced into Pichia yeast GS115 (manufactured by Invitrogen Corp.) using electroporation. The vector-introduced Pichia yeast GS115 was cultured in a G418-containing medium free from histidine to obtain several clones having the MK gene of interest. The obtained clones were cultured, while induced with methanol. The culture supernatant was collected, and western blotting using rabbit anti-mouse MK polyclonal antibodies was conducted to confirm whether the clones secreted MK.

One of the clones that secreted MK into the culture supernatant by the induction was designated as T3L-50-4P, and this clone was cultured (see Japanese Patent Laid-Open No. 7-39889). The MK secretion products were collected from the culture supernatant and subjected to purification by ion-exchange chromatography and affinity chromatography using a heparin column to obtain highly pure MK.

Cell Line

The UMR-106 rat osteosarcoma cell line was originally obtained from the American Type Culture Collection, PO Box 1549, Manassas, Va., USA as a frozen stock (catalog no. CRL-1661; batch no. 58494148).

Cell Culture Media and Reagents

The cells were maintained in: DMEM+Glutamax (DMEM, catalog no. 10569-010 500 mL, lot. no. 778325, Invitrogen/Gibco) supplemented with the following items: Penicillin (10,000 U/mL stock concentration)—Streptomycin (10,000 µg/mL stock concentration) (catalog no. 15140-122 100 mL, lot no. 730849, Invitrogen/Gibco) at a rate of 1 mL/200 mL of DMEM 10% fetal bovine serum (FBS, catalog no. 100099-141, lot no. 6955347Y, Invitrogen/Gibco). The DEM+Glutamax media containing 50 U/mL penicillin, 50 µg/mL streptomycin and 10% FBS is identified as Complete media in this report. The 10% FBS was replaced by 0.3% (w/v) bovine serum albumin (BSA) for the cell migration assays. The BSA was supplied by Sigma-Aldrich, catalog no. A-3192, lot no. 31K1264 and was formulated as a 15% (w/v) stock solution in D-PBS which was sterilized by passage through a 0.22 micron filter and stored at −20° C. prior to use. The cell cultures were maintained in T75 tissue culture-treated flasks in a humidified incubator at approximately 37° C. and 5% carbon dioxide. Cells were sub-cultured twice weekly at a sub-culture ratio ranging from approximately 1:8 to 1:20. Cells were dissociated from the flask by rinsing once with Dulbecco's phosphate buffered saline (DPBS, catalog no. 14190, lot no. 783715, Invitrogen/Gibco) and then incubated with 0.25% Trypsin-EDTA solution (Invitrogen/Gibco) at 37° C. for 2-5 minutes. The cells were then removed by addition of approximately 10 mL of Complete media. The experiments were completed using UMR-106 cells at ~50 to 75% confluency on the day prior to assay. These cultures were washed once with DMEM and cultured overnight in DMEM containing 0.5% FBS. On the day of the experiment the cells were removed from the culture flask by trypsin-EDTA treatment, the trypsin was then quenched by the addition or DMEM+0.5% FBS or DMEM+1% BSA and washed at least once with DMEM+0.3% BSA. The cells were then resuspended in DMEM+0.3% BSA at a final concentration 105 cells per 0.3 mL.

Equipment

The cell migration assays were performed using the following modified Boyden Chamber kits supplied by Millipore Australia: QCM Chemotaxis Cell Migration Assay, 24-well (8 µm pores), colormetric (catalog no. ECM 508).

Test and Reference Article Formulation

An aliquot of the 4.69 mg/mL midkine stock solution was thawed at room temperature on the day of the first experiment. On each day of use this stock solution was diluted at the rate of 4.3 uL per 1.0 mL in D-PBS under aseptic conditions at ambient temperature. The resulting 20 µg/mL solution was used immediately for coating the inserts. The unused midkine stock at 4.69 mg/mL was retained at 2-8° C. for use in subsequent experiments.

On the day of the first experiment an aliquot of each of the test compounds was diluted in D-PBS to a final concentration of 2 mg/mL. These working stocks were then be further diluted in DMEM/0.3% BSA to the final concentrations of antibody used in the assays (ranging from 10 to 100 µg/mL). The 2 mg/mL working stocks were retained at 2-8° C. for use in subsequent experiments. The control mouse IgG1 protein was reconstituted in 2.65 mL of sterile water with gentle rotation of the vial until the powder dissolves completely. The resulting 2 mg/mL stock solution was further diluted in DMEM/0.3% BSA to the final concentrations of antibody used in the assays (ranging from 10 to 100 µg/mL). Unused stock solution of the IgG1 protein was aliquoted and stored frozen at approximately −20° C. for the study duration. PBS vehicle control treatments were prepared by dilution of D-PBS at a 1 in 20 (v/v) ratio in DMEM/0.3% BSA.

Study Design

A total of three migration assay experiments were completed for each antibody. Briefly, the undersides of the transwell filter inserts were pre-coated with recombinant midkine protein (20 ug/mL). The inserts were then washed and placed into wells containing control and test treatments (i.e., anti-midkine antibodies) and the UMR-106 cells added to the upper chamber of the inserts. The extent of UMR-106 cell migration to the lower face of the insert was assessed after a four hour assay period. Assay readouts were manual counts of the number of cells present on the lower surface.

Cell Migration Assay Method

The experiments were completed using ~80% confluent UMR-106 cells. On the day prior to assay, growth media from the cultures were removed and the cells were washed once with DMEM only and cultured overnight in DMEM containing 0.5% FBS. On the day of experiment the cells were removed from the culture flask by trypsin-EDTA treatment, centrifuged to pellet and washed once with DMEM only. The cells were then resuspended in DMEM+ 0.3% BSA (sterile filtered) for seeding into the well inserts from the cell migration assay kit. The cell migration assays were performed using the following modified Boyden Chamber kits supplied by Millipore Australia: QCM Chemotaxis Cell Migration Assay, 24-well (8 µm pores), colorimetric (catalog no. ECM 508). This assay method is based on the manufacturers' instructions and the results of the previous method development/validation study at the test facility. QCM Chemotaxis Cell Migration Assay, 24-well (8 µm pores)

Protocol

1. Immediately prior to use the midkine protein was diluted to the target concentration of 20 µg/mL in D-PBS (by addition of 4.3 µL of MK 17 protein per 1.0 mL of DPBS.
2. The midkine was then immobilized on the underside (outside) face of the membrane of the QCM plate inserts by placing each inserts into wells containing either 0.3 mL of D-PBS or 0.3 mL of D-PBS containing 20 µg/mL of D-PBS. The inserts were then incubated at room temperature for one to two hours.
3. The plate inserts were then rinsed twice with D-PBS by serial transfer into two wells containing approximately 0.5 mL of D-PBS only
4. The plate inserts were then placed into 24-well plates containing 0.5 mL of DMEM+0.3% BSA per well plus or minus control and test treatments (i.e., anti-midkine antibodies IP10, IP14, IP14-H6L8, IP14-H5L8 and IP14-H6L3). Triplicate wells were used in each treatment.
5. $10^5$ UMR-106 cells, suspended in a volume of 0.3 mL of DMEM+0.3% BSA, were added to the upper (inside) chamber of the QCM plate inserts.
6. The plate was then covered and incubated for 4 hours at 37° C. in a humidified incubator with 5% $CO_2$.
7. The cells/media from the top side of the insert were carefully removed by pippeting out the remaining suspension (in experiments 2-4 the cells around the inside perimeter of the insert were also removed using a low pressure suction pump). The insert was then placed into a clean well containing 400 µL of Cell Stain and incubated for 20 minutes at room temperature.
8. The insert was then rinsed sequentially in three beakers of water.
9. While the insert was still moist, a cotton-tip swab was used to gently remove any non-migratory cells from the interior of the insert. The procedure was then repeated with a second, clean cotton-tipped swab.
10. The insert was allowed to dry.
11. The number of cells on each insert was then estimated by counting the total number of cells in two to four fields at 100× magnification under an inverted microscope (using a Millar's ocular grid to facilitate cell counts)

Data Calculation and Analysis

The mean background OD 560 nm readings obtained for reagent blanks in the absence of cells were subtracted from each test result using Microsoft Excel 2003 spreadsheets (www.microsoft.com). Microsoft Excel 2003 spreadsheets were also used for calculation of group mean and standard deviation values for both readouts. Assay results were represented graphically using GraphPad Prism version 5.01 for Windows, GraphPad Software, San Diego Calif. USA, www.graphpad.com"

Results

The results are shown in Table 9 and FIG. 4. The anti-midkine MAbs IP-10, IP-14, IP14-H6L8, IP14-H5L8 and IP14-H6L3 inhibited UMR-106 cell migration by an average of 53.7%, 18.0%, 38.7%, 40.7% and 44.3% respectively. These results show that the humanised IP14 antibodies IP14-H6L8, IP14-H5L8 and IP14-H6L3 inhibited UMR-106 cell migration with greater efficacy that the murine IP14 precursor antibody.

TABLE 9

UMR106 cell migration inhibition by anti-MK antibodies

| Treatment | MK-17 (μg/mL) | Mean Cells/Field | | | % Inhibition | | | Mean % Inhibition |
|---|---|---|---|---|---|---|---|---|
| | | Assay 4 | Assay 5 | Assay 6 | Assay 4 | Assay 5 | Assay 6 | |
| D-PBS | 0 | 6 ± 1.6 | 6 ± 0.2 | 3 ± 0.2 | — | — | — | — |
| D-PBS | 20 | 48 ± 1.6*** | 42 ± 8.5*** | 42 ± 4.5*** | 0 | 0 | 0 | 0 |
| IP-10, 100 ug/mL | 20 | 18 ± 4.6*** | 22 ± 5.4*** | 21 ± 2.4*** | 63 | 48 | 50 | 53.67 ± 4.70*** |
| IP-14, 100 ug/mL | 20 | 45 ± 4.1 | 38 ± 0.9 | 26 ± 13.5*** | 6 | 10 | 38 | 18.00 ± 10.07 |
| IP14 H6L8, 100 ug/mL | 20 | 27 ± 0.2*** | 32 ± 1.4* | 22 ± 0.2*** | 44 | 24 | 48 | 38.67 ± 7.42** |
| IP14 H5L8, 100 ug/mL | 20 | 19 ± 3.8*** | 29 ± 0.5*** | 29 ± 5.5** | 60 | 31 | 31 | 40.67 ± 9.67** |
| IP14 H6L3, 100 ug/mL | 20 | 25 ± 1.9*** | 25 ± 8.5*** | 23 ± 1.6*** | 48 | 40 | 45 | 44.33 ± 2.33*** |

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An isolated antibody comprising:
   (i) an immunoglobulin heavy chain comprising a variable region comprising an amino acid sequence set forth in SEQ ID NO: 6 or SEQ ID NO:7; and
   (ii) an immunoglobulin light chain comprising a variable region comprising an amino acid sequence set forth in SEQ ID NO: 17;
   wherein the antibody binds human midkine (huMK) protein.

2. The antibody according to claim 1, wherein:
   (i) the immunoglobulin heavy chain comprises a variable region comprising an amino acid sequence set forth in SEQ ID NO: 6; and
   (ii) the immunoglobulin light chain comprises a variable region comprising an amino acid sequence set forth in SEQ ID NO: 17.

3. The antibody according to claim 1, wherein:
   (i) the immunoglobulin heavy chain comprises a variable region comprising an amino acid sequence set forth in SEQ ID NO: 7; and
   (ii) the immunoglobulin light chain comprises a variable region comprising an amino acid sequence set forth in SEQ ID NO: 17.

4. The antibody according to claim 1, which is a four-polypeptide chain structure consisting of two heavy and two light chains, a single chain antibody, diabody, triabody or tetrabody.

5. The antibody according to claim 1, which is an antibody fragment which binds huMK.

6. The antibody of claim 5, wherein the fragment is a Fab fragment or single domain antibody.

7. The antibody according to claim 1, wherein the binding affinity of the antibody for huMK is greater than the binding affinity of the corresponding murine IP14 precursor antibody for huMK under equivalent conditions, wherein the murine IP14 precursor antibody comprises (i) an immunoglobulin heavy chain comprising a variable region comprising an amino acid sequence set forth in SEQ ID NO:1 and (ii) an immunoglobulin light chain comprising a variable region comprising an amino acid sequence set forth in SEQ ID NO:9.

8. A conjugate comprising an antibody according to claim 1 and a compound which is directly or indirectly bound to the antibody.

9. The conjugate of claim 8, wherein the compound is selected from the group consisting of a radioisotope, a detectable label, a therapeutic agent, a colloid, a toxin, a nucleic acid, a peptide, a protein, a compound that increases the half-life of the antibody in a subject and mixtures thereof.

10. The conjugate of claim 9, wherein the therapeutic agent is selected from the group consisting of: a cytotoxin, a radioisotope, an immunomodulatory agent, an anti-angiogenic agent, a toxin, an anti-proliferative agent, a pro-apoptotic agent, a chemotherapeutic agent, and a therapeutic nucleic acid.

11. The conjugate of claim 10, wherein the chemotherapeutic agent is carboplatin.

12. The conjugate according to claim 8, wherein the compound is indirectly bound to the antibody via a linker.

13. A pharmaceutical composition comprising an antibody according to claim 1 and a pharmaceutically acceptable carrier.

14. The pharmaceutical composition according to claim 10, comprising a further therapeutic agent selected from the group consisting of: a cytotoxin, a radioisotope, an immunomodulatory agent, an anti-angiogenic agent, a toxin, an anti-proliferative agent, a pro-apoptotic agent, a chemotherapeutic agent, and a therapeutic nucleic acid.

15. The pharmaceutical composition according to claim 14, wherein the chemotherapeutic agent is carboplatin.

16. The pharmaceutical composition according to claim 13 and an anti-cancer agent.

17. A kit comprising:
   (i) a first container comprising an antibody according to claim 1; and
   (ii) a second container comprising a compound selected from the group consisting of a radioisotope, a detectable label, a therapeutic agent, a colloid, a toxin, a nucleic acid, a peptide, a protein, a compound that increases the half-life of the antibody in a subject and mixtures thereof.

18. The kit of claim 17, wherein the therapeutic agent is selected from the group consisting of: a cytotoxin, a radioisotope, an immunomodulatory agent, an anti-angiogenic agent, a toxin, an anti-proliferative agent, a pro-apoptotic agent, a chemotherapeutic agent, and a therapeutic nucleic acid.

19. The kit according to claim 17, wherein the therapeutic agent is an anti-cancer agent.

20. An isolated and/or recombinant polynucleotide encoding an antibody according to claim 1.

21. A vector comprising a polynucleotide of claim 20.

22. A host cell comprising a polynucleotide of claim 20.

23. A method for producing an antibody that binds human midkine (huMK) protein, said method comprising:
   culturing a host cell of claim 17 for a time and under conditions sufficient for the host cell to produce the antibody; and optionally
   (ii) recovering the antibody produced at (i) from the cell culture;
   wherein the antibody produced at (i) comprises:
      (a) an immunoglobulin heavy chain comprising a variable region comprising an amino acid sequence set forth in SEQ ID NO: 6 or 7; and
      (b) an immunoglobulin light chain comprising a variable region comprising an amino acid sequence set forth in SEQ ID NO: 17.

24. A method for inhibiting an interaction between human midkine and a ligand thereof, said method comprising exposing a human subject or a biological sample obtained therefrom to an antibody according to claim 1.

25. A method for inhibiting human midkine activity, said method comprising exposing a human subject or a biological sample obtained therefrom to an antibody according to claim 1.

26. A method for treating or preventing a midkine-related disease or disorder in a subject in need thereof, said method comprising administering to the subject an antibody according to claim 1.

27. The method of claim 26, wherein the midkine-related disease or disorder is an autoimmune disease, cancer, or an inflammatory disease.

28. The method of claim 27, wherein the inflammatory disease is multiple sclerosis.

29. The method of claim 26, wherein the midkine-related disease or disorder is cancer.

30. The method according to claim 29, further comprising administering to the subject a chemotherapeutic agent.

31. The method according to claim 30, wherein the chemotherapeutic agent is carboplatin.

32. The method according to claim 29, further comprising administering to the subject an anti-cancer agent.

* * * * *